US006967021B2

(12) United States Patent
Panjwani et al.

(10) Patent No.: US 6,967,021 B2
(45) Date of Patent: Nov. 22, 2005

(54) USE OF GALECTIN-3 TO PROMOTE THE RE-EPITHELIALIZATION OF WOUNDS

(75) Inventors: Noorjahan Panjwani, Medford, MA (US); Zhiyi Cao, Cambridge, MA (US)

(73) Assignee: Trustees of Tufts College, Boston, MA (US)

( * ) Notice: Subject to any disclaimer, the term of this patent is extended or adjusted under 35 U.S.C. 154(b) by 31 days.

(21) Appl. No.: 10/133,234

(22) Filed: Apr. 26, 2002

(65) Prior Publication Data

US 2004/0071684 A1 Apr. 15, 2004

Related U.S. Application Data

(60) Provisional application No. 60/286,903, filed on Apr. 27, 2001.

(51) Int. Cl.[7] .......................... A61K 39/00; A61K 38/00
(52) U.S. Cl. ........................ 424/185.1; 514/12; 514/23; 530/350
(58) Field of Search ........................... 424/184.1, 185.1; 514/12, 23; 530/350

(56) References Cited

U.S. PATENT DOCUMENTS 6,310,270 B1 * 10/2001 Huang et al.
2002/0044932 A1 * 4/2002 Liu et al.

OTHER PUBLICATIONS

Skolnick et al. From genes to protein structure and function: novel applications of computational approaches in the genomic era. Trends Biotechnol. 18(1):34–9, 2000.*

Attwood TK. Genomics. The Babel of bioinformatics. Science. 290(5491):471–473, 2000.*

Metzler et al . Solution structure of human CTLA–4 and delineation of a CD80/CD86 binding site conserved in CD28. Nat Struc Biol. 4(7):527–531, 1997.*

"The role of galectin–3 in corneal epithelial cell migration and wound healing", Cao et al. Abstract published in *Invest. Opth. Vis. Sci.*, 41:S682, 2000 (Mar.) and poster # B727 presented at the Annual Meeting of the Association for Research in Vision and Ophthalmology on May 3, 2000.

"The role of galectin–3 in corneal epithelial cell migration and wound healing", Cao et al. Abstract published in *Glycobiology*, 10:1088, 2000 (Oct.) and talk presented at the Annual Conference of the Society for Glycobiology on Nov. 11, 2000.

"Comparison of gene expression patterns of normal and healing corneas using cDNA microarrays", Cao et al. Abstract published in *Invest. Opth. Vis. Sci.*, 42:S584, 2001 (Mar.) and poster # B278 presented at the Annual Meeting of the Association for Research in Vision and Ophthalmology on May 2, 2001.

"Galectin–3 stimulates re–epithelialization of corneal wounds", Amin et al. Abstract published in *Invest. Opth. Vis. Sci.*, 42:S889, 2001 (Mar.) and poster # B789 presented at the Annual Meeting of the Association for Research in Vision and Ophthalmology on May 3, 2001.

"Impaired corneal epithelial wound closure in galectin–3 deficient mice", Panjwani et al. Abstract published in *Invest. Opth. Vis. Sci.*, 42:S936, 2001 (Mar.) and talk presented at the Annual Meeting of the Association for Research in Vision and Ophthalmology on May 4, 2001.

* cited by examiner

*Primary Examiner*—Christina Chan
*Assistant Examiner*—Maher Haddad
(74) *Attorney, Agent, or Firm*—Lawson & Weitzen, LLP; Sonia K. Guterman

(57) ABSTRACT

Methods for the therapeutic treatment of epithelial wounds in mammals comprising administering to a mammal afflicted with an epithelial wound a therapeutically effective amount of a galectin-3 protein and/or a galectin-7 protein are provided. Pharmaceutical compositions comprising a pharmaceutically suitable carrier or diluent and as an active agent a galectin-3 protein and/or a galectin-7 protein are also provided.

20 Claims, 16 Drawing Sheets

Human galectin-3 (SEQ ID NO.1):

```
  1 MADNFSLHDA LSGSGNPNPQ GWPGAWGNQP AGAGGYPGAS YPGAYPGQAP PGAYPGQAPP
 61 GAYHGAPGAY PGAPAPGVYP GPPSGPGAYP SSGQPSAPGA YPATGPYGAP AGPLIVPYNL
121 PLPGGVVPRM LITILGTVKP NANRIALDFQ RGNDVAFHFN PRFNENNRRV IVCNTKLDNN
181 WGREERQSVF PFESGKPFKI QVLVEPDHFK VAVNDAHLLQ YNHRVKKLNE ISKLGISGDI
241 DLTSASYTMI
```

Amino acid composition (250 amino acids, molecular wt: 26174.2 Da)

| aa | # | mole% | wt% |
|---|---|---|---|
| A Ala | 27 | 10.80 | 7.33 |
| C Cys | 1 | 0.40 | 0.39 |
| D Asp | 9 | 3.60 | 3.96 |
| E Glu | 6 | 2.40 | 2.96 |
| F Phe | 9 | 3.60 | 5.06 |
| G Gly | 34 | 13.60 | 7.41 |
| H His | 6 | 2.40 | 3.14 |
| I Ile | 10 | 4.00 | 4.32 |
| K Lys | 8 | 3.20 | 3.92 |
| L Leu | 15 | 6.00 | 6.49 |
| M Met | 3 | 1.20 | 1.51 |
| N Asn | 18 | 7.20 | 7.85 |
| P Pro | 36 | 14.40 | 13.36 |
| Q Gln | 9 | 3.60 | 4.41 |
| R Arg | 9 | 3.60 | 5.37 |
| S Ser | 14 | 5.60 | 4.66 |
| T Thr | 6 | 2.40 | 2.32 |
| V Val | 14 | 5.60 | 5.30 |
| W Trp | 3 | 1.20 | 2.13 |
| Y Tyr | 13 | 5.20 | 8.11 |

FIGURE 1

Human galectin-7 (SEQ ID NO.2):

```
  1 MSNVPHKSSL PEGIRPGTVL RIRGLVPPNA SRFHVNLLCG EEQGSDAALH FNPRLDTSEV
 61 VFNSKEQGSW GREERGPGVP FQRGQPFEVL IIASDDGFKA VVGDAQYHHF RHRLPLARVR
121 LVEVGGDVQL DSVRIF
```

Amino acid composition (136 amino acids, molecular wt: 15059.1 Da)

| aa |   | # | mole% | wt% |
|----|---|---|-------|-----|
| A | Ala | 7 | 5.15 | 3.30 |
| C | Cys | 1 | 0.74 | 0.68 |
| D | Asp | 7 | 5.15 | 5.35 |
| E | Glu | 9 | 6.62 | 7.72 |
| F | Phe | 8 | 5.88 | 7.82 |
| G | Gly | 14 | 10.29 | 5.31 |
| H | His | 6 | 4.41 | 5.46 |
| I | Ile | 5 | 3.68 | 3.76 |
| K | Lys | 3 | 2.21 | 2.55 |
| L | Leu | 12 | 8.82 | 9.02 |
| M | Met | 1 | 0.74 | 0.87 |
| N | Asn | 5 | 3.68 | 3.79 |
| P | Pro | 10 | 7.35 | 6.45 |
| Q | Gln | 6 | 4.41 | 5.11 |
| R | Arg | 13 | 9.56 | 13.48 |
| S | Ser | 10 | 7.35 | 5.78 |
| T | Thr | 2 | 1.47 | 1.34 |
| V | Val | 15 | 11.03 | 9.88 |
| W | Trp | 1 | 0.74 | 1.24 |
| Y | Tyr | 1 | 0.74 | 1.08 |

FIGURE 2

```
CLUSTAL W (1.81) Multiple Sequence Alignments

Sequence 1: Human galectin-3      250 aa    (SEQ ID NO.1)
Sequence 2: Rabbit galectin-3     242 aa    (SEQ ID NO.4)
Sequence 3: Chicken galectin-3    262 aa    (SEQ ID NO.5)
Sequence 4: Hamster galectin-3    245 aa    (SEQ ID NO.6)

Sequences (2:3) Aligned. Score: 58      Sequences (3:4) Aligned. Score: 52
Sequences (1:3) Aligned. Score: 55      Sequences (1:2) Aligned. Score: 82
Sequences (1:4) Aligned. Score: 84      Sequences (2:4) Aligned. Score: 78

Group 1: Sequences:   2     Score:4935
Group 2: Sequences:   3     Score:4768
Group 3: Sequences:   4     Score:3929
Alignment Score 6348

Human galectin-3      ----------------MADNFSLHDALSGSGNPNPQGWPGAWG-NQPAG  32
Hamster galectin-3    ----------------MADGFSLNDALAGSGNPNPQGWPGAWG-NQP-G  31
Rabbit galectin-3     ----------------MADGFSLNDALSGSGHPPNQGWPGPWG-NQPAG  32
Chicken galectin-3    MQAMKARCWQPHWMLPLLPLSSPLHPQLSDALPAHNPGAPPPQGWNRPPG  50
                                      :. . .*:  *:..  .  * * . * *:* *

Human galectin-3      AGGYPG-ASYPGAYPGQAPPGAYPGQAPPGAYPG--APGAYPGAPAPGVY  79
Hamster galectin-3    AGGYPG-ASYPGAYPGQAPPGAYPGQAPPGAYPGPTAPGAYPG-PAPGAY  79
Rabbit galectin-3     PGGYPG-AAYPGAYPGHAP-GAYPGQAPPGPYPG-------PG--AHGAY  71
Chicken galectin-3    PGAFPAYPGYPGAYP--GAPGPYPG--APGPHHG--PPGPYPG-GPPGPY  93
                      .*.:*. ..******  .. *.***  .**.:  *    **   . * *

Human galectin-3      PGPPSGPGAYPSSGQPSATGAYPA--TGPYG-APAGPLIVPYNLPLPGGV  126
Hamster galectin-3    PGQPGASGAYP-----SAPGAYPA--AGPYG-APTGALTVPYKLPLAGGV  121
Rabbit galectin-3     PGQPGGPGAYPSPGQPSGAGAYPG--ASPYS-ASAGPLPVPYDLPLPGGV  118
Chicken galectin-3    PGGP--PGPYPG----GPPGPYPGGPTAPYSEAPAAPLKVPYDLPLPAGL  137
                      **  *  .*.**      . *.**.  :.**. *.:..* ***.***..*:

Human galectin-3      VPRMLITILGTVKPNANRIALDFQRGNDVAFHFNPRFNENNRRVIVCNTK  176
Hamster galectin-3    MPRMLITIMGTVKPNANRIILNFLRGNDIAFHFNPRFNENNRRVIVCNTK  171
Rabbit galectin-3     MPRMLITIVGTVKPNANRLALDFKRGNDVAFHFNPRFNENNRRVIVCNTK  168
Chicken galectin-3    MPRLLITITGTVNSNPNRFSLDFKRGQDIAFHFNPRFKEDHKRVIVCNSM  187
                      :**:****.***:.*.**: *:* **:*:*********:*:::*****:

Human galectin-3      LDNNWGREERQS-VFPFESGKPFKIQVLVEPDHFKVAVNDAHLLQYNHRV  225
Hamster galectin-3    QDNNWGREERQS-AFPFESGRPFKIQVLVEADHFKVAVNDAHLLQYNHRM  220
Rabbit galectin-3     VDNNWGREERQT-TFPFEIGKPFKIQVLVEPDHFKVAVNDAHLLQYNHRM  217
Chicken galectin-3    FQNNWGKEERTAPRFPFEPGTPFKLQVLCEGDHFKVAVNDAHLLQFNFRE  237
                       :****:***  : **** ***:*** * * ***************:*.*

Human galectin-3      KKLNEISKLGISGDIDLTSASYTMI  250
Hamster galectin-3    KNLREINQMEISGDITLTSAAPTMI  245
Rabbit galectin-3     RNLKEINKLGISGDIQLTSASHAMI  242
Chicken galectin-3    KKLNGITKLCIAGDITLTSVLTSMI  262
                      ::*. *.:: *:*** ***. :**
```

FIGURE 3

```
CLUSTAL W (1.81) Multiple Sequence Alignments

Sequence 1: Human galectin-7      136 aa      (SEQ ID NO.2)
Sequence 2: Rat galectin-7        136 aa      (SEQ ID NO.7)
Sequence 3: Mouse galectin-7      136 aa      (SEQ ID NO.8)

Sequences (2:3) Aligned. Score:  88
Sequences (1:2) Aligned. Score:  72
Sequences (1:3) Aligned. Score:  78

Group 1: Sequences:    2      Score:2837
Group 2: Sequences:    3      Score:2646
Alignment Score 2151

Rat galectin-7      MSATHHKTPLPQGVRLGTVMRIRGVVPDQAGRFHVNLLCGEEQEADAALH 50
Mouse galectin-7    MSATHHKTSLPQGVRVGTVMRIRGLVPDQAGRFHVNLLCGEEQGADAALH 50
Human galectin-7    MSNVPHKSSLPEGIRPGTVLRIRGLVPPNASRFHVNLLCGEEQGSDAALH 50
                    **  . **:.**:*:* ***:****:** :*.************ :****

Rat galectin-7      FNPRLDTSEVVFNTKQQGKWGREERGTGIPFQRGQPFEVLIITTEEGFKT 100
Mouse galectin-7    FNPRLDTSEVVFNTKQQGKWGREERGTGIPFQRGQPFEVLLIATEEGFKA 100
Human galectin-7    FNPRLDTSEVVFNSKEQGSWGREERGPGVPFQRGQPFEVLIIASDDGFKA 100
                    *************.*:**.******.*:************:::::***:

Rat galectin-7      VIGDDEYLHFHHRMPSSNVRSVEVGGDVQLHSVKIF 136
Mouse galectin-7    VVGDDEYLHFHHRLPPARVRLVEVGGDVQLHSLNIF 136
Human galectin-7    VVGDAQYHHFRHRLPLARVRLVEVGGDVQLDSVRIF 136
                    *:**  :* **:**:* :.** *********.*:.**
```

FIGURE 4

PROSITE SCAN of Human galectin-3 (SEQ ID NO.1)

N-glycosylation site (PROSITE: PS00001)

4-7 NFSL (SEQ ID NO.9)

Protein kinase C phosphorylation site (PROSITE: PS00005)

137-139 TVK (SEQ ID NO.10)
194-196 SGK (SEQ ID NO.11)

Casein kinase II phosphorylation site (PROSITE: PS00006)

6-9 SLHD (SEQ ID NO.12)
175-178 TKLD (SEQ ID NO.13)

N-myristoylation site (PROSITE: PS00008)

24-29 GAWGNQ (SEQ ID NO.14)
27-32 GNQPAG (SEQ ID NO.15)
34-39 GGYPGA (SEQ ID NO.16)
43-48 GAYPGQ (SEQ ID NO.17)
52-57 GAYPGQ (SEQ ID NO.18)
61-66 GAYPGA (SEQ ID NO.19)
65-70 GAPGAY (SEQ ID NO.20)
68-73 GAYPGA (SEQ ID NO.21)

Galaptin signature sequence (PROSITE: PS00309)

181-200 WGREERQSVFPFESGKPFKI (SEQ ID NO.22)

FIGURE 5

PROSITE SCAN of Human galectin-7 (SEQ ID NO.2)

N-glycosylation site (PROSITE: PS00001)

29-32 NASR (SEQ ID NO.23)

Protein kinase C phosphorylation site (PROSITE: PS00005)

132-134 SVR (SEQ ID NO.24)

Casein kinase II phosphorylation site (PROSITE: PS00006)

9-12 SLPE (SEQ ID NO.25)

N-myristoylation site (PROSITE: PS00008)

13-18 GIRPGT (SEQ ID NO.26)
44-49 GSDAAL (SEQ ID NO.27)

Galaptin signature sequence (PROSITE: PS00309)

70-89 WGREERGPGVPFQRGQPFEV (SEQ ID NO.28)

FIGURE 6

```
PFAM 7.0 HMM Sequence Alignment

PF00337 (Galactoside-binding lectin domain, SEQ ID NO.3)
score 217.2, E = 1.3e-62

PF00337              *->pglvalnlglkpGktltVkGtVapknakrFavNlgkgskEEndlvLH
                        p+  +l++g+ p++ +t+ GtV p na+r a+++ +g   nd+++H
Human galectin-3 117  PYNLPLPGGVVPRMLITILGTVKP-NANRIALDFQRG----NDVAFH 158

PF00337              fNPRFneaHGDqntvVcNSkenGDNeWGtEqReaafPFqaGqpFeisIsv
                     fNPRFne +   +++VcN+k+++  +WG E+R+  fPF++G+pF+i++ v
Human galectin-3 159 FNPRFNENN--RRVIVCNTKLDN--NWGREERQSVFPFESGKPFKIQVLV 204

PF00337              eedkfkVkvndghefeFphRlk.leavqyLgikGDikltsikf<-*
                     e+d+fkV+vnd+h+++++hR k+l ++++Lgi+GDi+lts+++
Human galectin-3 205 EPDHFKVAVNDAHLLQYNHRVKkLNEISKLGISGDIDLTSASY      247
```

FIGURE 7

```
PFAM 7.0 HMM Sequence Alignment

PF00337 (Galactoside-binding lectin domain, SEQ ID NO.3)
score 124.0, E = 1.6e-34

PF00337                *->pglvalnlglkpGktltVkGtVapknakrFavNlgkgskEEndlvLH
                          p + l++g +pG  l+++G+V p na rF+vNl+ g     +d +LH
Human galectin-7    5  PHKSSLPEGIRPGTVLRIRGLVPP-NASRFHVNLLCGEEQGSDAALH  50

PF00337                fNPRFneaHGDqntvVcNSkenGDNeWGtEqReaafPFqaGqpFeisIsv
                       fNPR + +       vV NSke G  +WG E+R +  PFq+GqpFe+ I
Human galectin-7   51  FNPRLDTSE-----VVFNSKEQG--SWGREERGPGVPFQRGQPFEVLIIA  93

PF00337                eedkfkVkvndghefeFphRlkleavqyLgikGDikltsikf<-*
                        d fk  v d+ + +F hRl+l +v  +++ GD+ l+s+ +
Human galectin-7   94  SDDGFKAVVGDAQYHHFRHRLPLARVRLVEVGGDVQLDSVRI      135
```

Microarray data

| Gene | Fold △ |
|---|---|
| Galectin-7 | 11.7 ↑ |
| GAPDH | 1.0 (NC) |
| RPS29 | 1.1 ↑ |
| ODC | 1.2 ↑ |

B

Semi-quantitative RT-PCR

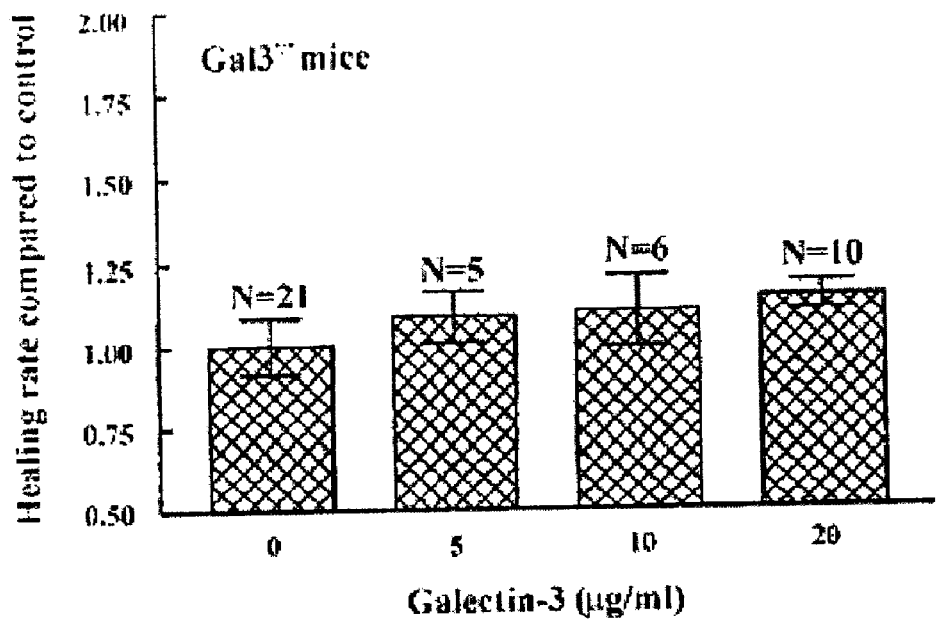
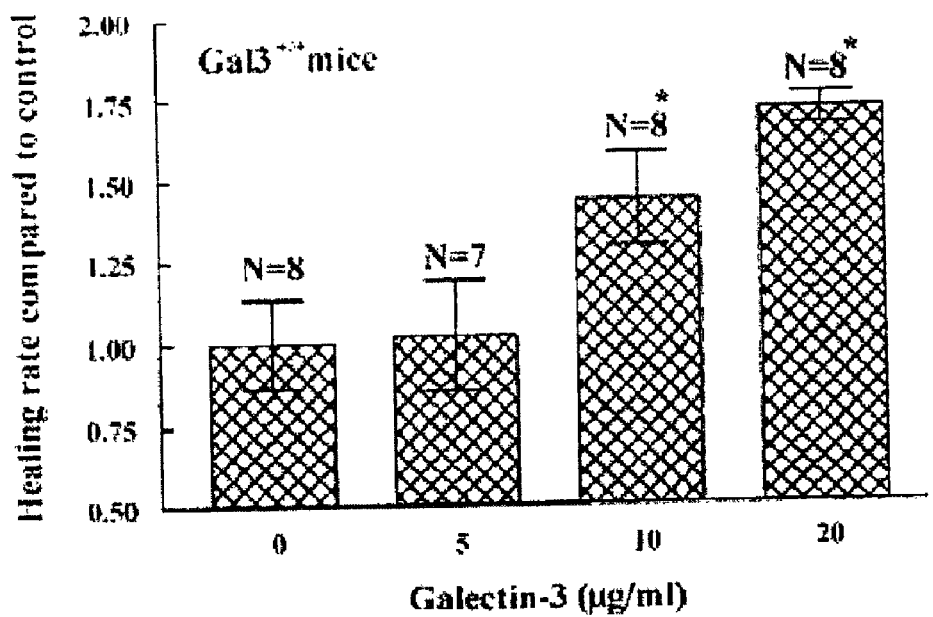
FIGURE 14

A
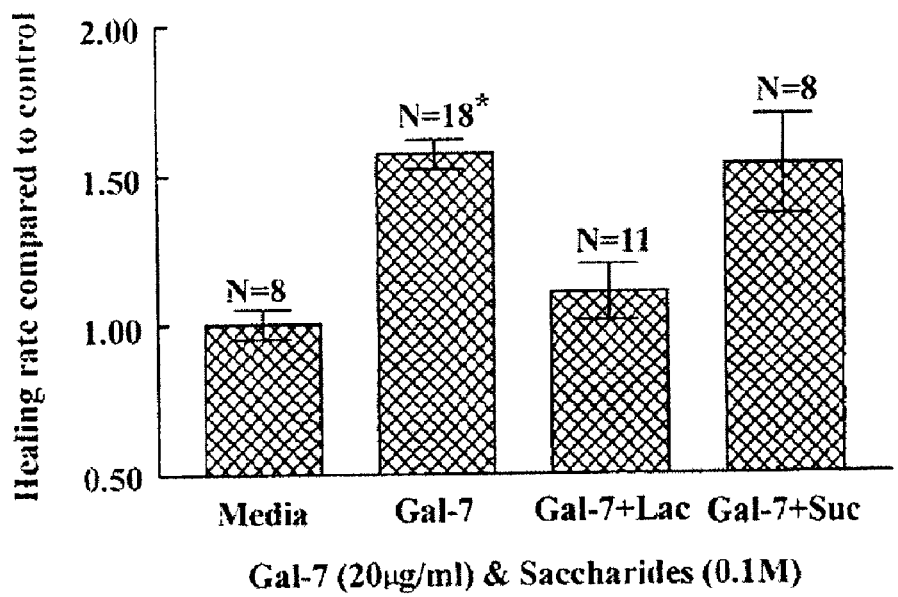
B
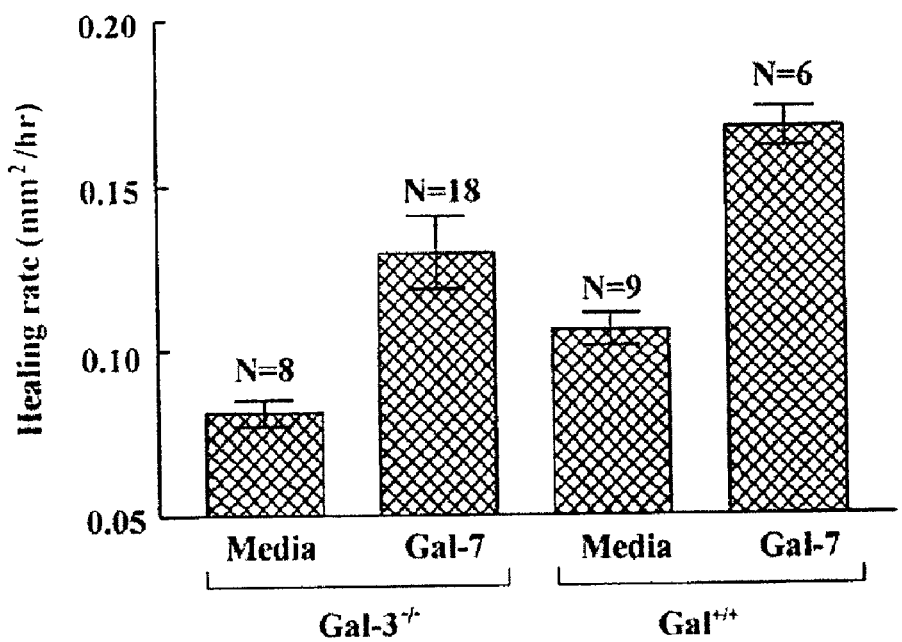
FIGURE 16

USE OF GALECTIN-3 TO PROMOTE THE RE-EPITHELIALIZATION OF WOUNDS

RELATED APPLICATIONS

The present application claims priority to provisional application U.S. Ser. No. 60/286,903, filed Apr. 27, 2001 which is incorporated herein by reference in its entirety.

GOVERNMENT FUNDING

This invention was made with Government support under grant number EY-07088 from the National Institutes of Health. Accordingly, the government may have certain rights in this invention.

BACKGROUND OF THE INVENTION

The repair of wounds in mammalian tissue (e.g., epithelial defects, lesions, or erosions caused by disease, accidental injury, surgical procedure, etc.) involves an orderly, controlled cellular response. Three phases have been described in normal wound healing: acute inflammatory phase, extracellular matrix and collagen synthesis, and remodeling (*Wound Repair* by Peacock, W. B. Saunders, Philadelphia, Pa., 1984). The sequence of the healing process is initiated during an acute inflammatory phase with the deposition of provisional tissue. This is followed by re-epithelialization, collagen synthesis and deposition, fibroblast proliferation, and neovascularization, all of which ultimately define the remodeling phase (see, for example, Clark, *J. Am. Acad. Dermatol.* 13:701, 1985). These events are known to be influenced by growth factors and cytokines secreted by inflammatory cells and by epithelial cells, endothelial cells, platelets, and fibroblasts localized at the edges of the wound (see, for example, *The Molecular and Cellular Biology of Wound Repair* (*The Language of Science*) Ed. by Clark, Plenum Press, New York, N.Y., 1996; Hunt et al., in *The Surgical Wound* Ed. by Dineen at al., Lea & Febiger, Philadelphia, Pa., 1981; Nemeth et al., in *Growth Factors and Other Aspects of Wound Healing: Biological and Clinical Implications* Ed. by Barbul et al., A. R. Liss, New York, N.Y., 1988; and Assoian et al., *Nature* 309:804, 1984). During re-epithelialization, cells at the leading edge undergo a phenotypic conversion characterized by a dramatic reorganization of the cytoskeleton, disruption of stable intercellular adhesion, and redistribution of adhesion related molecules. The breakage of the stable intercellular contacts is a prerequisite for initiating re-epithelialization. Following re-epithelialization, reversion to the epithelial phenotype, including the reformation of stable intercellular contacts, must occur if the function of the epithelium is to be fully restored. The failure of epithelial cells to migrate over the wound surface and failure of migrated epithelial cells to remain adherent to the substratum are fundamental causes of debilitating clinical conditions known as persistent epithelial defects (i.e., non healing defects) and recurrent epithelial erosions respectively.

Disorders of wound healing constitute a serious medical problem for several different organ systems including the skin, gastrointestinal tract, and cornea. For example, loss of cell-cell adhesions within the epidermis produces life-threatening blistering skin diseases known as pemphigus foliaceus and pemphigus vulgaris (*Cell Adhesion and Human Disease* Ed. by Marsh et al., Ciba Foundation Symposium, Vol. 189, John Wiley & Sons, New York, N.Y., 1995). Persistent epithelial defects in the form of delayed re-epithelialization are a characteristic of chronic skin wounds, in particular venous stasis ulcers (Falanga et al., *J. Dermatol. Surg. Oncol.* 19:764, 1993). Within the cornea, lack of epithelial cell adhesion to the stroma and the basement membrane leads to recurrent corneal erosions (Macaluso et al., in *Cornea* Ed. by Krachmer, Mosby, St. Louis Mo., 1997). Persistent corneal epithelial defects occur in a wide variety of clinical situations such as in injuries caused by radiation, corneal abrasions or lacerations, chemical burns of the cornea such as alkali and acid burns, keratopathies, keratities and corneal dystrophies. Persistent corneal epithelial defects carry a high risk of corneal perforation and ulceration (Macaluso et al., supra).

Despite the need for more rapid healing of wounds, to date there has been only limited success in accelerating wound healing with pharmaceutical agents. In the case of corneal injuries, the use of epidermal growth factor (Eiferman et al., *Invest. Ophthalmol. Vis. Sci.* (Suppl.) 28:52, 1987), fibronectin (Nishida et al., *J. Cell. Biol.* 97:1653, 1983), collagenase inhibitors (Kenyon et al., *Invest. Ophthalmol. Vis. Sci.* 18:570, 1979), topical steroids (Lass et al., *Arch. Ophthalmol.* 99:673, 1981), matrix metalloproteinase inhibitors (Murphy et al., *Biochemistry* 30:8097, 1991), ascorbates (Foster et al., *Invest. Ophthalmol. Vis. Sci.* (Suppl.) 19:227, 1980), heparin (Aronson, *Am. J. Ophthalmol.* 70:65, 1970), and tetracyclines (Perry et al., *Ophthalmology* (Suppl.) 92:77, 1985) does not always result in successful long-term management. For example, topical application to a corneal injury of epidermal growth factor (EGF) (Singh et al., *Am. J. Ophthalmol.* 103:802, 1987) or fibronectin (Tenn et al., *Invest. Ophthalmol. Vis. Sci.* (Suppl.) 26:92, 1985), enhances epithelial wound healing but does not prevent recurrent erosion and secondary breakdown of the corneal epithelial surface.

Accordingly, there is a need in the art for additional pharmaceutical agents and compositions that promote the healing of wounds. In particular, there is a need for agents, compositions and therapeutic methods that promote the re-epithelialization of persistent epithelial defects and prevent recurrent epithelial erosions.

SUMMARY OF THE INVENTION

In one aspect, the present invention provides methods for the therapeutic treatment of epithelial injuries in mammalian tissue involving administering to a mammal afflicted with an epithelial injury a therapeutically effective amount of galectin-3, galectin-7, or a combination of galectin-3 and galectin-7.

In another aspect, the present invention provides pharmaceutical compositions that include a pharmaceutically acceptable carrier or diluent and an amount of galectin-3 and/or galectin-7 sufficient to promote the re-epithelialization of wounds in injured mammalian tissues.

In general, it is believed that galectin-3 and/or galectin-7 will be clinically useful in promoting the healing of wounds associated with any epithelial tissue including but not limited to the skin epithelium; the corneal epithelium; the lining of the gastrointestinal tract; the lung epithelium; and the inner surface of kidney tubules, of blood vessels, of the uterus, of the vagina, of the urethra, or of the respiratory tract. The present invention encompasses the treatment of a variety of wounds that include but are not limited to persistent epithelial defects and recurrent epithelial erosions such as surgical wounds, excisional wounds, blisters, ulcers, lesions, abrasions, erosions, lacerations, boils, cuts, sores, and burns resulting from heat exposure or chemicals. These wounds may be in normal individuals or those subject to conditions which induce abnormal wound healing such as diabetes, corneal dystrophies, uremia, malnutrition, vitamin deficiencies, obesity, infection, immunosuppression and complications associated with systemic treatment with steroids, radiation therapy, non-steroidal anti-inflammatory drugs (NSAID), anti-neoplastic drugs and anti-metabolites.

In certain embodiments, the present invention involves the administration of pharmaceutical compositions that include galectin-3 proteins with the amino acid sequence of human galectin-3 as represented by SEQ ID NO:1 of the sequence listing. In other embodiments, the present invention involves the administration of pharmaceutical compositions that include galectin-3 proteins with an amino acid sequence that is substantially identical to the amino acid sequence of SEQ ID NO:1. For example, in certain embodiments, the present invention involves the administration of pharmaceutical compositions that include galectin-3 proteins which contain accidentally or deliberately induced alterations, such as deletions, additions, substitutions or modifications of the amino acid residues of SEQ ID NO:1. In yet other embodiments, the present invention involves the administration of pharmaceutical compositions that include proteins represented by fragments of the amino acid sequence SEQ ID NO:1 or hybrid proteins that comprise these fragments. Fragments of SEQ ID NO:1 preferably include a galectin-3 N-terminal domain and a galectin-3 proline, glycine, and tyrosine-rich domain; a galectin-3 proline, glycine, and tyrosine-rich domain and a galectin-3 galactoside-binding domain; or a galectin-3 galactoside-binding domain.

In certain other embodiments, the present invention involves the administration of pharmaceutical compositions that include galectin-7 proteins with the amino acid sequence of human galectin-7 as represented by SEQ ID NO:2 of the sequence listing. In other embodiments, the present invention involves the administration of pharmaceutical compositions that include galectin-7 proteins with an amino acid sequence that is substantially identical to the amino acid sequence of SEQ ID NO:2. For example, in certain embodiments, the present invention involves the administration of pharmaceutical compositions that include galectin-7 proteins which contain accidentally or deliberately induced alterations, such as deletions, additions, substitutions or modifications of the amino acid residues of SEQ ID NO:2. In yet other embodiments, the present invention involves the administration of pharmaceutical compositions that include proteins represented by fragments of the amino acid sequence SEQ ID NO:2 or hybrid proteins that comprise these fragments. Preferred fragments of SEQ ID NO:2 include a galectin-7 galactoside-binding domain.

The present invention also encompasses the administration of pharmaceutical compositions that include proteins represented by the amino acid sequence of galectin-3 and/or galectin-7 taken from any mammalian species including but not limited to bovine, canine, feline, caprine, ovine, porcine, murine, and equine species.

In certain embodiments, the pharmaceutical compositions of the present invention further include one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

The pharmaceutical compositions of the present invention can be administered to humans and other mammals topically, orally, rectally, parenterally, intracisternally, intravaginally, intraperitoneally, bucally, ocularly, or nasally, depending on the severity and location of the wound being treated. Administration may be therapeutic or it may be prophylactic. Liquid dosage forms for oral administration of an inventive pharmaceutical composition include, but are not limited to, pharmaceutically acceptable emulsions, microemulsions, solutions, suspensions, syrups and elixirs. Solid dosage forms for oral administration include capsules, tablets, pills, powders, and granules. Dosage forms for topical or transdermal administration include ointments, pastes, creams, lotions, gels, powders, solutions, sprays, inhalants, or patches. Injectable preparations may be in the form of sterile injectable aqueous or oleaginous suspensions. Compositions for rectal or vaginal administration are preferably suppositories. Prophylactic formulations may be present or applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area. The invention includes ophthalmological devices, surgical devices, audiological devices or products which contain disclosed pharmaceutical compositions (e.g., gauze bandages or strips).

DESCRIPTION OF THE DRAWING

FIG. 1 depicts the amino acid sequence and composition of human galectin-3 (Accession No. BAA22164 in GenBank, SEQ ID NO:1).

FIG. 2 depicts the amino acid sequence and composition of human galectin-7 (Accession No. I55469 in GenBank, SEQ ID NO:2).

FIG. 3 depicts a CLUSTAL W alignment of the amino acid sequence of human galectin-3 (SEQ ID NO:1) with the amino acid sequences of rabbit galectin-3 (Accession No. JC4300 in GenBank), chicken galectin-3 (Accession No. AAB02856 in GenBank), and hamster galectin-3 (Accession No. CAA55479 in GenBank). The first (upper) sequence in the figure is amino acids 1 to 250 of human galectin-3 (SEQ ID NO:1), the second sequence in the figure is amino acids 1 to 245 of hamster galectin-3, the third sequence in the figure is amino acids 1 to 242 of rabbit galectin-3, and the fourth (lower) sequence in the figure is amino acids 1 to 262 of chicken galectin-3.

FIG. 4 depicts a CLUSTAL W alignment of the amino acid sequence of human galectin-7 (SEQ ID NO:2) with the amino acid sequences of rat galectin-7 (Accession No. P97590 in GenBank) and mouse galectin-7 (Accession No. O54974 in GenBank). The first (upper) sequence in the figure is amino acids 1 to 136 of rat galectin-7, the second sequence in the figure is amino acids 1 to 136 of mouse galectin-7, and the third (lower) sequence in the figure is amino acids 1 to 136 of human galectin-7 (SEQ ID NO:2).

FIG. 5 is a summary of the results of a PROSITE scan of human galectin-3 (SEQ ID NO:1).

FIG. 6 is a summary of the results of a PROSITE scan of human galectin-7 (SEQ ID NO:2).

FIG. 7 depicts an alignment of the galactoside-binding domain of human galectin-3 with a consensus amino acid sequence (PF00337) derived from a hidden Markov model (HMM) from PFAM. The upper sequence is the consensus amino acid sequence (PF00337, SEQ ID NO:3), while the lower amino acid sequence corresponds to amino acids 117 to 247 of SEQ ID NO:1.

FIG. 8 depicts an alignment of the galactoside-binding domain of human galectin-7 with a consensus amino acid sequence (PF00337) derived from a hidden Markov model (HMM) from PFAM. The upper sequence is the consensus amino acid sequence (PF00337, SEQ ID NO:3), while the lower amino acid sequence corresponds to amino acids 5 to 135 of SEQ ID NO:2.

FIG. 14 is a graph illustrating the effect of exogenous galectin-3 on the healing rate of injured corneal epithelium in (A) galectin-3 deficient (gal-3$^{-/-}$) mice and (B) wild type (gal-3$^{+/+}$) mice.

FIG. 16 includes (A) a graph illustrating the effect of exogenous galectin-7 on the healing rate of injured corneal epithelium in wild type (gal-3$^{+/+}$), when used alone, with β-lactose (Lac), or with sucrose (Suc); and (B) a graph comparing the effect of exogenous galectin-7 on the healing rate of injured corneal epithelium in wild type (gal-3$^{+/+}$) and galectin-3 deficient (gal-3$^{-/-}$) mice.

DESCRIPTION OF CERTAIN PREFERRED EMBODIMENTS

Figure 9:
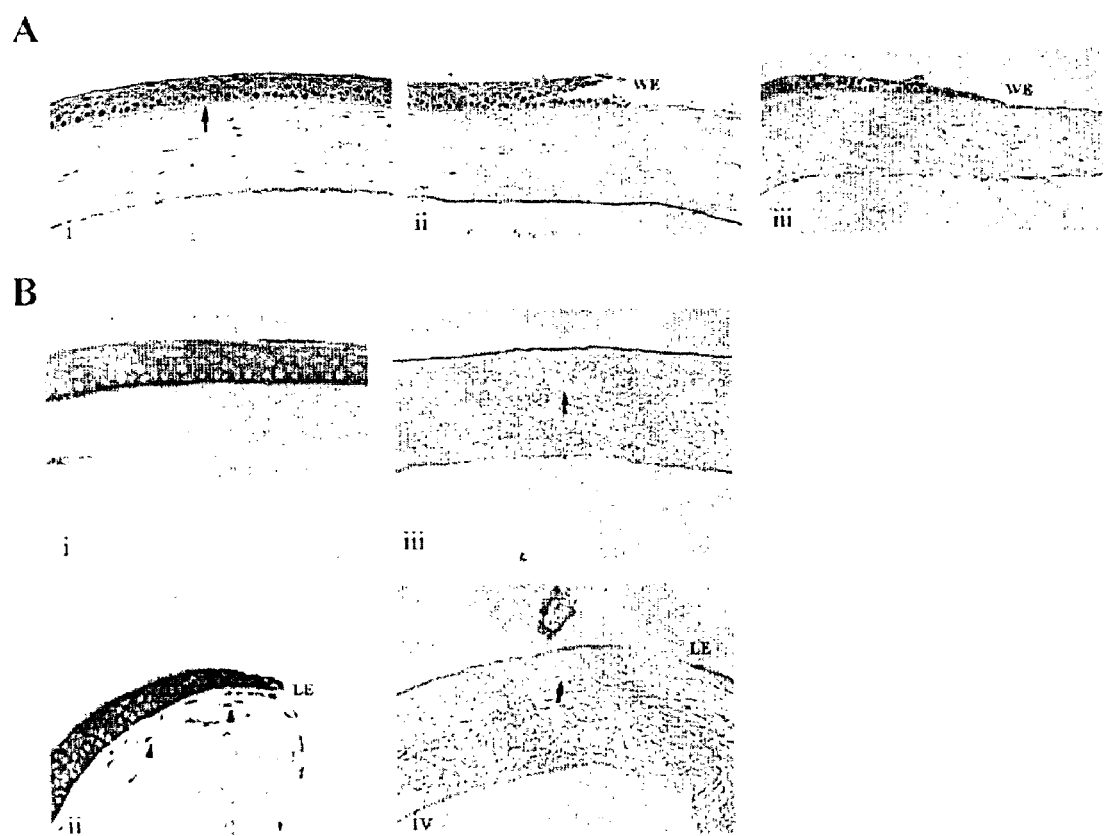
FIG. 9 includes a series of photographs of corneas with 2 mm abrasion or excimer laser wounds that were allowed to partially heal in vivo and were then analyzed for galectin-3 immunoreactivity in paraffin sections. (A), Hematoxylin and eosin staining of (i) normal corneas and corneas immediately after (ii) abrasion and (iii) excimer laser injury. (B), Immunohistochemical staining of (i) normal gal3$^{+/+}$ corneas and (ii) healing gal3$^{+/+}$ corneas after excimer laser injury. Immunohistochemical staining of (iii) normal gal3$^{-/-}$ corneas and (iv) healing gal3$^{-/-}$ corneas after excimer laser injury. Dark color indicates positive immunostaining. WE, wound edge; LE, leading edge of migrating epithelium; arrows, epithelium; arrowheads, leukocytes/stromal cells.

The present application mentions various patents, scientific articles, and other publications. The contents of each such item are hereby incorporated by reference. In addition, the contents (as of the filing date of the application) of all websites referred to herein are incorporated by reference.

The present invention provides pharmaceutical compositions comprising galectin-3 and/or galectin-7 useful for enhancing the re-epithelialization of wounds in injured mammalian tissues. The invention also provides methods for the therapeutic treatment of epithelial injuries in mammalian tissue comprising administering to a mammal afflicted with an epithelial injury a therapeutically effective amount of galectin-3, galectin-7, or a combination of galectin-3 and -7. When administering a combination of galectin-3 and -7, galectin-3 may be administered before, in conjunction with, or after the administration of galectin-7.

The invention encompasses the finding that galectin-3 is up-regulated in migrating corneal epithelial cells following injury to the cornea (Example 1). The invention also includes the discovery that the re-epithelialization of corneal transepithelial excimer laser wounds and corneal alkali-burn wounds is significantly slower in galectin-3-deficient mice compared to that in wild type mice (Example 2). The invention further provides the discovery that the expression of a number of injury-related genes (e.g., tolloid-like protein and galectin-7) are abnormal in galectin-3-deficient mice (Example 3). Additionally, the invention demonstrates that exogenous galectin-3 and -7 promote the re-epithelialization of corneal wounds (Examples 4 and 5, respectively).

Galectins

Lectins are proteins that are defined by their ability to bind carbohydrates specifically and to agglutinate cells (see, for example, Sharon, *Trends Biochem. Sci.* 18:221, 1993). Lectins have been shown to be involved in a wide variety of cellular functions including cell-cell and cell-matrix interactions. Lectins are widespread among plants, invertebrates and mammals. Animal lectins have been grouped into four distinct families: 1) C-type lectins; 2) P-type lectins; 3) galectins (formerly termed S-type lectins); and 4) pentraxins (see, for example, Barondes et al., *J. Biol. Chem.* 269:20807, 1994).

All mammalian galectins that have been analyzed in detail recognize β-lactose and related β-galactosides. While all mammalian galectins share similar affinity for small β-galactosides, they show significant differences in binding specificity for more complex glycoconjugates (Henrick et al., *Glycobiology* 8:45, 1998; Sato et al., *J. Biol. Chem.* 267:6983, 1992; and Seetharaman et al., *J. Biol. Chem.* 273:13047, 1998). In addition to binding β-galactoside sugars, galectins possess hemagglutination activity. Laminin, a naturally occurring glycoprotein containing numerous polylactosamine chains, has been shown to be a natural ligand for certain galectins. Laminin is a component of the basal laminae, the extracellular matrix which underlies all epithelia and surrounds individual muscle, fat and Schwann cells. Interactions between cells and the basal laminae are known to influence the migration and/or differentiation of various cell types during mammalian development. Galectins do not contain traditional sequences that specify membrane translocation, but are both secreted and located intracellularly. In addition to their affinity for β-galactoside sugars, members of the galectin family share significant sequence similarity in the carbohydrate recognition domain (CRD; also referred to as the carbohydrate-binding domain), the relevant amino acid residues of which have been determined by X-ray crystallography (Lobsanov et al., *J. Biol. Chem.* 267:27034, 1993 and Seetharaman et al., supra). Galectins have been implicated in a wide variety of biological functions including cell adhesion (Cooper et al., *J. Cell Biol.* 115:1437, 1991), growth regulation (Wells et al., *Cell* 64:91, 1991), cell migration (Hughes, *Curr. Opin. Struct. Biol.* 2:687, 1992), neoplastic transformation (Raz et al., *Int. J. Cancer* 46:871, 1990) and immune responses (Offner et al., *J. Neuroimmunol.* 28:177, 1990). There are presently 12 characterized eukaryotic members of the galectin family.

Galectin-3

Members of the galectin-3 family of proteins (previously known as CBP-35, Mac-2, L-34, εBP, and RL-29) typically include between about 240 and 270 amino acids and have molecular weights that range between about 25 and 29 kDa. Galectin-3 proteins are generally composed of a short N-terminal domain, a C-terminal domain which includes a galactoside-binding region, and an intervening proline, glycine, and tyrosine-rich domain which includes repeats of 7–10 conserved amino acids (Liu et al., *Biochemistry* 35:6073, 1996 and Cherayil et al., *Proc. Natl. Acad. Sci. USA*, 87:7324, 1990). The tandem repeats are similar to those found in the collagen gene superfamily. The number of repeats varies between galectin-3 proteins and accounts for the differences in size between galectin-3 proteins from different species. The N-terminal domain of galectin-3 permits the protein to undergo multimerization upon binding to surfaces containing glycoconjugate ligands.

Galectin-3 is expressed in various inflammatory cells (e.g., activated macrophages, basophils, and mast cells) and in epithelia and fibroblasts of various tissues (Perillo et al., *J. Mol. Med.* 76:402, 1998). It is found on the cell surface, within the extracellular matrix (ECM), in the cytoplasm, and in the nucleus of cells. On the cell surface or in the ECM galectin-3 is thought to mediate cell-cell and cell-matrix interactions by binding to complementary glycoconjugates containing polylactosamine chains found in many ECM and cell surface molecules. Galectin-3 is thought to inhibit cell-matrix adhesion by binding to laminin. In the nucleus of cells galectin-3 may influence cell-matrix interactions indirectly by influencing the expression of well-known cell adhesion molecules (e.g., α6β1 and α 4β7 integrins, Warlfield et al., *Invasion Metastasis* 17:101, 1997 and Matarrese et al., *Int. J. Cancer* 85:545, 2000) and cytokines (e.g., IL-1, Jeng et al., *Immunol. Lett.* 42:113, 1994). Galectin-3 expression is developmentally regulated in selected organs such as the kidney and its expression level in pulmonary alveolar epithelial cells and hepatocytes is up-regulated following injury. Galectin-3 has been shown to concentrate in the nucleus of certain cell types during proliferation. Expression of galectin-3 is elevated in certain tumors, suggesting galectin-3 plays a role in metastasis. Indeed, overexpression of galectin-3 in a weakly metastatic cell line caused a significant increase in metastatic potential (Raz et al., supra).

Human galectin-3 is 250 amino acids long and has an approximate molecular weight of 26.1 kDa (SEQ ID NO:1, FIG. 1). As illustrated in FIGS. 1, 3, 5, and 7, human galectin-3 contains the following domains, signature sequences, or other structural features (for general information regarding PS and PF prefix identification numbers, refer to Sonnhammer et al., *Protein* 28:405, 1997): an N-terminal domain located at about amino acid residues 1 to 14 of SEQ ID NO:1; a proline, glycine, and tyrosine-rich domain located at about amino acid residues 15 to 116 of SEQ ID NO:1; a galactoside-binding domain located at about amino acid residues 117 to 247 of SEQ ID NO:1; a galaptin signature sequence (PROSITE No. PS00309) located at about amino acids 181 to 200 of SEQ ID NO:1; one potential N-glycosylation site (PROSITE No. PS00001) located at about amino acids 4 to 7 of SEQ ID NO:1; two potential protein kinase C phosphorylation sites (PROSITE No. PS00005) located at about amino acids 137 to 139 and 194 to 196 of SEQ ID NO:1; two potential casein kinase II phosphorylation sites (PROSITE No. PS00006) located at about amino acids 6 to 9 and 175 to 178 of SEQ ID NO:1; and eight potential myristoylation sites (PROSITE No. PS00008) located at about amino acids 24 to 29, 27 to 32, 34 to 39, 43 to 48, 52 to 57, 61 to 66, 65 to 70, and 68 to 73 of SEQ ID NO:1.

As defined herein, a "galectin-3 protein" may include a galectin-3 "N-terminal domain", a galectin-3 "proline, glycine, and tyrosine-rich domain", and/or a galectin-3 "galactoside-binding domain". These domains are further defined as follows.

As used herein, a galectin-3 "N-terminal domain" includes an amino acid sequence of about 10–20 amino acids, preferably about 14 amino acids that shares at least about 60%, 70%, 80%, 90%, 95%, 99%, or 100% identity with amino acids 1 to 14 of SEQ ID NO:1. The N-terminal domain can include an N-glycosylation site (PROSITE No. PS00001) and/or a casein kinase II phosphorylation site (PROSITE No. PS00006). The PROSITE N-glycosylation site has the consensus sequence: N-{P}-[ST]-{P} and the PROSITE casein kinase II phosphorylation site has the consensus sequence: [ST]-X(2)-[DE]. In the above consensus sequences, and other motifs or signature sequences described herein, the standard IUPAC one-letter code for the amino acids is used. Each element in the pattern is separated by a dash (-); square brackets ([ ]) indicate the particular residues that are accepted at that position; X indicates that any residue is accepted at that position; and numbers in parentheses (( )) indicate the number of residues represented by the accompanying amino acid. In certain embodiments, the N-terminal domain includes amino acids L7 and L11 of SEQ ID NO:1. As shown in FIG. 3, these amino acids are conserved across several mammalian species of galectin-3 and may therefore play a catalytic and/or structural role.

As used herein, a galectin-3 "proline, glycine, and tyrosine-rich domain" includes an amino acid sequence of about 60 to 140 amino acids, more preferably about 80 to 120 amino acids, or about 90 to 110 amino acids that shares at least about 60%, 70%, 80%, 90%, 95%, 99%, or 100% identity with amino acids 15 to 116 of SEQ ID NO:1. The proline, glycine, and tyrosine-rich domain can also include one, two, three, four, five, six, seven, or eight N-myristoylation sites (PROSITE No. PS00008) which have the consensus sequence: G-{EDRKHPFYW}-X(2)-[STAGCN]-{P}. In certain embodiments, the proline, glycine, and tyrosine-rich domain includes the following amino acids and regions of SEQ ID NO:1: G21, P23, G27, N28, P30, G32, G34, P37, Y41–P46, G53, Y55–G57, P61, G62, G66, P72, G73, G77, Y79–G81, P83, G87, Y89, P90, G99, Y101, P102, P106, Y107, A109, L114, and V116. These amino acids and regions are conserved across several mammalian species of galectin-3 and may play a catalytic and/or structural role (see amino acids indicated with a "*" in FIG. 3).

As used herein, a galectin-3 "galactoside-binding domain" includes an amino acid sequence of about 80 to 180 amino acids having a bit score for the alignment of the sequence to the consensus sequence PF00337 from PFAM (SEQ ID NO:3) of at least 150. Preferably, a galectin-3 galactoside-binding domain includes at least about 100 to 160 amino acids, more preferably about 110 to 150 amino acids, or about 120 to 140 amino acids and has a bit score for the alignment of the sequence to the consensus sequence PF00337 from PFAM (SEQ ID NO:3) of at least 150, more preferably at least 175, most preferably 200 or greater.

To calculate the bit score for the alignment of a particular sequence to the consensus sequence PF00337 from PFAM, the sequence of interest can be searched against the PFAM database of HMMs (e.g., the PFAM database, release 2.1) using the default parameters available at www.sanger.ac.uk/Software/Pfam. A description of the PFAM database can be found in Sonnhammer et al., supra and a detailed description of HMMs can be found, for example, in Gribskov et al., *Meth. Enzymol.* 183:146, 1990 and Stultz et al., *Protein Sci.* 2:305, 1993.

The galectin-3 galactoside-binding domain can further include one, preferably two, protein kinase C phosphorylation sites (PROSITE No. PS00005); a casein kinase II phosphorylation site (PROSITE No. PS00006); and/or a galaptin signature sequence (PROSITE No. PS00309). The protein kinase C phosphorylation site has the following consensus sequence: [ST]-X-[RK]. The galaptin signature sequence has the following consensus sequence: W-[GEK]-X-[EQ]-X-[KRE]-X(3,6)-[PCTF]-[LIVMF]-[NQEGSKV]-X-[GH]-X(3)-[DENKHS]-[LIVMFC]. In certain embodiments, the galectin-3 galactoside-binding domain includes the following amino acids and regions of SEQ ID NO:1: P117, Y118, L120–L122, G125, P128, R129, L131–134, G136–V138, N141, N143, R144, L147, F149, R151, G152, D154, A156–F163, E165, R169–N174, N179–G182, E184–R186, F190–E193, G195, P197–K199, Q201–L203, E205, D207–Q220, N222, R224, L228, I231, I236, G238–I240, and L242–S244. These amino acids and regions are conserved across several mammalian species of galectin-3 and may play a catalytic and/or structural role (see amino acids indicated with a "*" in FIG. 3).

Certain galectin-3 proteins of the present invention include the amino acid sequence of human galectin-3 as represented by SEQ ID NO:1. Other galectin-3 proteins of the present invention include an amino acid sequence that is substantially identical to the amino acid sequence of SEQ ID NO:1. The term "substantially identical" is used herein to refer to a first amino acid that contains a sufficient or minimum number of amino acid residues that are identical to aligned amino acid residues in a second amino acid sequence such that the first and second amino acid sequences can have a common structural domain and/or common functional activity. For example, amino acid sequences that contain a common structural domain having at least about 60%, or 65% identity, preferably at least 75% identity, more preferably at least 85%, 90%, 91%, 92%, 93%, 94%, 95%, 96%, 97%, 98%, or 99% identity to SEQ ID NO:1 are termed substantially identical to the amino acid sequence of SEQ ID NO:1. In particular, proteins which contain accidentally or deliberately induced alterations, such as deletions, additions, substitutions or modifications of certain amino acid residues of SEQ ID NO:1 may fall within the definition of galectin-3 proteins provided herein. It will also be appreciated that as defined herein, galectin-3 proteins may include regions represented by the amino acid sequence of galectin-3 taken from other mammalian species including but not limited to bovine, canine, feline, caprine, ovine, porcine, murine, and equine species.

Calculations of sequence identity between sequences are performed as follows. To determine the percent identity of two amino acid sequences, the sequences are aligned for optimal comparison purposes (e.g., gaps can be introduced in one or both of a first and a second amino acid sequence for optimal alignment). The amino acid residues at corresponding amino acid positions or nucleotide positions are then compared. When a position in the first sequence is occupied by the same amino acid residue or nucleotide as the corresponding position in the second sequence, then the proteins are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using an alignment software program using the default parameters. Suitable programs include, for example, CLUSTAL W by Thompson et al., *Nuc. Acids Research* 22:4673, 1994 (www.ebi.ac.uk/clustalw), BL2SEQ by Tatusova and Madden, *FEMS Microbiol. Lett.* 174:247, 1999 (www.ncbi.nlm.nih.gov/blast/bl2seq/bl2.html), SAGA by Notredame and Higgins, *Nuc. Acids Research* 24:1515, 1996 (igs-server.cnrs-mrs.fr/~cnotred), and DIALIGN by Morgenstern et al., *Bioinformatics* 14:290, 1998 (bibiserv.techfak.uni-bielefeld.de/dialign).

Galectin-7

Members of the galectin-7 family of proteins typically exist as monomers that include between about 130 and 140 amino acids and have molecular weights that range between about 15 and 16 kDa (see, for example, Magnaldo et al., *Develop. Biol.* 168:259, 1995 and Madsen et al., *J. Biol. Chem.* 270:5823, 1995). The expression of galectin-7 has been associated with the onset of epithelial stratification (Timmons et al., *Int. J. Dev. Biol.* 43:229, 1999). Galectin-7 is thought to play a role in cell-matrix and cell-cell interactions. Galectin-7 is found in areas of cell-cell contact (e.g., in the upper layers of human epidermis); its expression is sharply downregulated in anchorage independent keratinocytes and it is absent in a malignant keratinocyte cell line. Galectin-7 may be required for the maintenance of normal keratinocytes (see, Madsen et al., supra).

Human galectin-7 includes 136 amino acids and has an approximate molecular weight of 15.1 kDa (SEQ ID NO:2, FIG. 2). As illustrated in FIGS. 2, 4, 6, and 8, human galectin-7 contains the following domains, signature sequences, or other structural features: a galactoside-binding domain located at about amino acid residues 5 to 135 of SEQ ID NO:2; a galaptin signature sequence (PROSITE No. PS00309) located at about amino acids 70 to 89 of SEQ ID NO:2; one N-glycosylation site (PROSITE No. PS00001) located at about amino acids 29 to 32 of SEQ ID NO:2; one protein kinase C phosphorylation site (PROSITE No. PS00005) located at about amino acids 132 to 134 of SEQ ID NO:2; one casein kinase II phosphorylation site (PROSITE No. PS00006) located at about amino acids 9 to 12 of SEQ ID NO:2; and two myristoylation sites (PROSITE No. PS00008) located at about amino acids 13 to 18 and 44 to 49 of SEQ ID NO:2.

As defined herein, a "galectin-7 protein" includes a galectin-7 "galactoside-binding domain". This domain is further defined as follows.

As used herein, a galectin-7 "galactoside-binding domain" includes an amino acid sequence of about 80 to 180 amino acids having a bit score for the alignment of the sequence to the consensus sequence PF00337 from PFAM (SEQ ID NO:3) of at least 80. Preferably, a galectin-7 galactoside-binding domain includes at least about 100 to 160 amino acids, more preferably about 110 to 150 amino acids, or about 120 to 140 amino acids and has a bit score for the alignment of the sequence to the consensus sequence PF00337 from PFAM (SEQ ID NO:3) of at least 80, more preferably at least 100, most preferably 120 or greater. The galectin-7 galactoside-binding domain can include one N-glycosylation site (PROSITE No. PS00001); one protein kinase C phosphorylation site (PROSITE No. PS00005); one casein kinase II phosphorylation site (PROSITE No. PS00006); one or two myristoylation sites (PROSITE No. PS00008); and/or a galaptin signature sequence (PROSITE No. PS00309). In certain embodiments, the galectin-7 galactoside-binding domain includes the following amino acids and regions of SEQ ID NO:2: M1, S2, H6, K7, L10, P11, G13, R15, G17–V19, R21–G24, V26, P27, A30, R32–Q43, D46–N63, K65, Q67, G68, W70–G76, G78, P80–L90, I92, G97–K99V101, G103, D104, Y107, H109, F110, H112, R113, P115, V119, R120, V122L130, S132, I135, and F136. These amino acids and regions are conserved across several mammalian species of galectin-7 and may play a catalytic and/or structural role (see amino acids indicated with a "*" in FIG. 4).

Certain galectin-7 proteins of the present invention include the amino acid sequence of human galectin-7 as represented by SEQ ID NO:2. Other galectin-7 proteins of the present invention include an amino acid sequence that is substantially identical to the amino acid sequence of SEQ ID NO:2. In particular, proteins which contain accidentally or deliberately induced alterations, such as deletions, additions, substitutions or modifications of certain amino acid residues of SEQ ID NO:2 may fall within the definition of galectin-7 provided herein. It will also be appreciated that as defined herein, galectin-7 proteins may include regions represented by the amino acid sequence of galectin-7 taken from other mammalian species including but not limited to bovine, canine, feline, caprine, ovine, porcine, murine, and equine species.

Preparation of Galectin-3 and Galectin-7

It will be appreciated by one of ordinary skill in the art, that the galectins of this invention can be obtained from any available source. These include but are not limited to proteins isolated from natural sources, produced recombinantly or produced synthetically, e.g., by solid phase procedures. In accordance with the present invention, polynucleotide sequences which encode galectin-3 or galectin-7 may be used in recombinant DNA molecules that direct the expression of the galectins of this invention in appropriate host cells. Cherayil et al., supra and Madsen et al., supra, describe in detail the cloning of human galectin-3 and -7 respectively. In order to express a biologically active galectin-3 or galectin-7, the nucleotide sequence encoding galectin-3, galectin-7, or their functional equivalent, is inserted into an appropriate expression vector, i.e., a vector which contains the necessary elements for the transcription and translation of the inserted coding sequence. Methods which are well known to those skilled in the art can be used to construct expression vectors containing a galectin-3-encoding or galectin-7-encoding sequence and appropriate transcriptional or translational controls. These methods include in vitro recombinant DNA techniques, synthetic techniques and in vivo recombination or genetic recombination. The introduction of deletions, additions, or substitutions can be achieved using any known technique in the art e.g., using PCR based mutagenisis. Such techniques are described in Sambrook et al., *Molecular Cloning: A Laboratory Manual*, Cold Spring Harbor Press, Plainview, N.Y., 1989 and Ausubel et al., *Current Protocols in Molecular Biology*, John Wiley & Sons, New York, N.Y., 1989. A variety of expression vector/host systems may be utilized to contain and express a galectin-3-encoding or galectin-7-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. Alternatively, the galectins of the present invention could be produced using chemical methods to synthesize a galectin-3 or galectin-7 amino acid sequence, whole or in part. For example, peptide synthesis can be performed using various solid-phase techniques (Roberge et al., *Science* 269:202, 1995) and automated synthesis may be achieved, for example, using the 431A peptide synthesizer (available from Applied Biosystems of Foster City, Calif.) in accordance with the instructions provided by the manufacturer.

Pharmaceutical Compositions

In one aspect of the present invention, pharmaceutical compositions are provided, wherein these compositions comprise galectin-3 and/or galectin-7, and optionally comprise a pharmaceutically acceptable carrier. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, according to the methods of treatment of the present invention, the re-epithelialization of wounds is promoted by contacting the wounds with a pharmaceutical composition, as described herein. Thus, the invention provides methods for the treatment of wounds comprising administering a therapeutically effective amount of a pharmaceutical composition comprising active agents that include galectin-3 and/or galectin-7 to a subject in need thereof, in such amounts and for such time as is necessary to achieve the desired result. It will be appreciated that this encompasses administering an inventive pharmaceutical as a therapeutic measure to promote the re-epithelialization of a wound or as a prophylactic measure to minimize complications associated with the slow re-epithelialization of wounds (e.g., as a wound irrigation solution during and/or following surgery). In certain embodiments of the present invention a "therapeutically effective amount" of the pharmaceutical composition is that amount effective for promoting the re-epithelialization of a wound. The compositions, according to the method of the present invention, may be administered using any amount and any route of administration effective for healing a wound. Thus, the expression "amount effective for promoting the re-epithelialization of a wound", as used herein, refers to a sufficient amount of composition to heal a wound. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., wound size and location; age, weight and gender of the patient; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, parenterally, intracisternally, intravaginally, intraperitoneally, bucally, ocularly, or nasally, depending on the severity and location of the wound being treated.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples, galectin-3 and galectin-7 are useful as promoters of the re-epithelialization of wounds. In general, it is believed that these galectins will be clinically useful in stimulating the healing of wounds associated with any epithelial tissue including but not limited to the skin epithelium; the corneal epithelium; the lining of the gastrointestinal tract; the lung epithelium; and the inner surface of kidney tubules, of blood vessels, of the uterus, of the vagina, of the urethra, or of the respiratory tract. The present invention encompasses the treatment of a variety of epithelial wound types including but not limited to surgical wounds, excisional wounds, blisters, ulcers, lesions, abrasions, erosions, lacerations, boils, cuts, sores, and burns resulting from heat exposure or chemicals. These wounds may be in normal individuals or those subject to conditions which induce abnormal wound healing such as diabetes, corneal dystrophies, uremia, malnutrition, vitamin deficiencies, obesity, infection, immunosuppression and complications associated with systemic treatment with steroids, radiation therapy, non-steroidal anti-inflammatory drugs (NSAID), anti-neoplastic drugs and anti-metabolites.

Galectin-3 and/or galectin-7 could, for example, be used to promote dermal re-establishment subsequent to dermal loss. Alternatively, galectin-3 and/or galectin-7 could be used to increase the adherence of skin grafts to a wound bed and to stimulate re-epithelialization from the wound bed. Suitable skin grafts include, but are not limited to, autografts, artificial skin, allografts, autodermic grafts, autoepidermic grafts, avacular grafts, Blair-Brown grafts, bone grafts, brephoplastic grafts, cutis grafts, delayed grafts, dermic grafts, epidermic grafts, fascia grafts, full thickness grafts, heterologous grafts, xenografts, homologous grafts, hyperplastic grafts, lamellar grafts, mesh grafts, mucosal grafts, Ollier-Thiersch grafts, omenpal grafts, patch grafts, pedicle grafts, penetrating grafts, split skin grafts, and thick split grafts.

Galectin-3 and/or galectin-7 could be used to treat dermatitis herpetiformis in which blisters form at the dermo-epidermal junction. Galectin-3 and/or galectin-7 could be used to treat epidermolysis bullosa, a defect in adherence of the epidermis to the underlying dermis which results in frequent, open and painful blisters, by accelerating re-epithelialization of these lesions. Galectin-3 and/or galectin-7 could further be used to treat pemphigus diseases that involve loss of cell-cell adhesion within the epidermis, or pemphigoid diseases that involve loss of cell-cell adhesion at the dermo-epidermal junction. Galectin-3 and/or galectin-7 could be used to treat a variety of ulcers including but not limited to diabetic ulcers, dermal ulcers, decubitus ulcers, arterial ulcers, and venous stasis ulcers.

The present invention encompasses methods for the promotion of corneal tissue healing. This includes treating corneal epithelial defects caused by corneal ulcers, heat, radiation, phlyctenulosis, corneal abrasions or lacerations, photorefractive surgery for corrective myopia, foreign bodies and sterile corneal infiltrates; chemical burns caused by exposure to acids or alkali (e.g., hydrofluoric acid, formic acid, anhydrous ammonia, cement, and phenol) or other chemical agents such as white phosphorus, elemental metals, nitrates, hydrocarbons, and tar; keratopathies such as neurotrophic keratopathy, diabetic keratopathy and Thygeson's superificial punctate keratopathy; keratities such as viral keratitis (e.g., metaherpetic or herpetic keratitis) and bacterial keratitis; and corneal dystrophies such as lattice dystrophy, epithelial basement membrane dystrophy (EBMD) and Fuch's endothelial dystrophy.

Galectin-3 and/or galectin-7 could also be used to treat gastrointestinal ulcers and help heal the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, galectin-3 and galectin-7 could be used to promote the resurfacing of the mucosal surface to aid more rapid healing and to prevent or attenuate progression of inflammatory bowel disease. Galectin-3 and galectin-7 would be expected to bind mucin and facilitate its adhesion to the apical surface of the epithelium and could therefore be used to protect the gastrointestinal tract from injurious substances that are ingested or following surgery. Galectin-3 and/or galectin-7 could be used to reduce the side effects of gut toxicity that result from the treatment of bacterial infections, viral infections, radiation therapy, chemotherapy or other treatments. Galectin-3 and/or galectin-7 may, for example, be used prophylactically or therapeutically to prevent or attenuate mucositis, esophagitis, or gastritis (e.g., to heal lesions associated with oral, esophageal, intestinal, colonic, rectal, and anal ulcers).

Galectin-3 and/or galectin-7 could be used to promote urothelial healing. Tissue layers comprising urothelial cells may be damaged by numerous mechanisms including catheterization, surgery, or bacterial infection (e.g., infection by an agent which causes a sexually transmitted disease, such as gonorrhea). The present invention also encompasses methods for the promotion of tissue healing in the female genital tract comprising the administration of an effective amount of galectin-3 and/or galectin-7. Tissue damage in the female genital tract may be caused by a wide variety of conditions including Candida infections trichomoniasis, Gardnerella, gonorrhea, chlamydia, mycoplasma infections and other sexually transmitted diseases.

Galectin-3 and/or galectin-7 could be used to promote the repair of renal epithelial cells and, thus, could be useful for alleviating or treating renal diseases and pathologies such as acute and chronic renal failure and end stage renal disease. Galectin-3 and/or galectin-7 could be used to promote the repair of breast tissue and therefore could be used to promote healing of breast tissue injury due to surgery, trauma, or cancer. Galectin-3 and/or galectin-7 could further be used to promote healing and alleviate damage of brain tissue due to injury from trauma, surgery or chemicals.

Galectin-3 and/or galectin-7 could be administered prophylactically to reduce or prevent damage to the lungs caused by various pathological states. For example, galectin-3 and/or galectin-7 could be used to promote the repair of alveoli and bronchiolar epithelium to prevent, attenuate, or treat acute or chronic lung damage. Emphysema, which results in the progressive loss of alveoli, and inhalation injuries, i.e., resulting from smoke inhalation and burns, that cause necrosis of the bronchiolar epithelium and alveoli could be effectively treated using galectin-3 and/or galectin-7 as could damage attributable to chemotherapy, radiation treatment, lung cancer, asthma, black lung and other lung damaging conditions.

It will be appreciated that the therapeutic methods encompassed by the present invention are not limited to treating wounds in humans, but may be used to treat wounds in any mammal including but not limited to bovine, canine, feline, caprine, ovine, porcine, murine, and equine species. When treating wounds in a given species, it is preferred, but not required, that the galectin-3 and/or galectin-7 used, have an amino acid sequence that is substantially identical to the amino acid sequence of galectin-3 and/or galectin-7 as it occurs naturally in said species.

EXAMPLES

All animal treatments described in these examples conformed to the Association for Research in Vision and Ophthalmology Resolution on the Use of Animals in Vision Research and the recommendations of the NIH Guide for the Care and Use of Laboratory Animals.

Example 1

Up-regulation of Galectin-3 in Migrating Corneal Epithelium Following Injury

To determine whether the expression level of galectin-3 is altered in the epithelium of healing corneas following injury, mice corneas with 2 mm excimer laser ablations and abrasion wounds, were allowed to partially heal in vivo and were then processed for immunostaining with rat anti-human galectin-3 mAb M3/38 (American Type Culture Collection, Rockville, Md.). Corneal epithelium is a prototype-stratified squamous epithelium. In mouse, it constitutes 20–25% of total corneal thickness and is composed of 5 to 6 layers of cells. Posterior to the epithelial basement membrane is corneal stroma, which in mouse represents 70–80% of the total corneal thickness. Abrasion wounds remove epithelium leaving the corneal stroma intact. In contrast, excimer laser treatment, which is commonly used for correction of myopia, removes epithelium as well as anterior corneal stroma.

Swiss Webster mice (Taconic Laboratory Animal Services, Germantown, N.Y.) were anesthetized by an intramuscular injection of 1.25% avertin (0.2 ml/10 kg body weight). Avertin was prepared by mixing 2.5 g of 2,2,2 tribromoethanol, 5 ml 2-methyl-2-butanol (Aldrich, Milwaukee, Wis.) and 195 ml distilled water. Proparacaine eye drops (ALCAINE™ available from Alcon Labs, Fort Worth, Tex.) were applied to the cornea as topical anesthetic. Transepithelial excimer laser ablations were performed on the right eyes of a first group of mice (2 mm optical zone; 42 to 44 µm ablation depth, PTK mode) using an APEX PLUS™ excimer laser (Summit Technology of Waltham, Mass.). 2 mm abrasion wounds were produced on the right eyes of a second group of mice using an Alger brush (Alger Equipment Company of Lago Vista, Tex.).

Following surgery, all animals received an intramuscular injection of buprenorphine (0.2 ml of 0.3 mg/ml, BUPRENEX™ available from Reckitt & Colman Pharmaceuticals, Richmond, Va.) as a pain killer. Antibiotic ointment (VETROPOLYCIN™ available from Pharmaderm, Melville, N.Y.) was applied and the corneas were allowed to partially heal in vivo for 16 to 18 hours. At the end of the healing period the animals were anesthetized as described above and were sacrificed by cervical dislocation. The eyes were then fixed in formalin for two hours prior to embedding in paraffin wax. Tissue sections (5 μm thick) were cut in the place parallel to the ocular axis. The sections were deparaffinized by treatment with xyline and re-hydrated with graded ethanol solutions (100%, 70%, and 30%). For immunostaining, tissue sections were incubated sequentially with 3% $H_2O_2$ (37° C., 10 min), and 2.5% normal goat serum to block endogenous peroxidase activity and nonspecific binding, respectively. The sections were subsequently incubated with mAb M3/38 (undiluted hybridoma fluid, 1 hour), biotinylated anti-rat IgG for 1 hour (1:200, Vector Labs, Burlingame, Calif.), a freshly prepared complex of avidin D and biotinperoxidase for 20 hours (Vector Labs) and diaminobenzidine (DAB)—$H_2O_2$ reagent (Kirkegaard & Perry Labs, Gaithersburg, Md.). For negative controls, sections were treated with an irrelevant mAb or media alone.

As shown in FIG. 9, immunohistochemical staining of paraffin sections of normal (FIGS. 9A and B) and healing (FIGS. 9C and D) corneas indicated that in both models of corneal wound healing, the leading edge of the migrating epithelium of healing corneas stained more intensely with mAb M3/38 compared to the normal epithelium, especially in the basal and middle cell layers. In both healing as well as normal corneal epithelium, immunostaining was more intense at the site of cell-matrix attachment. While stromal cells of normal corneas did not react with mAb M3/38, cells in the anterior stroma under the healing corneas robustly expressed galectin-3, especially in the region under the migrating epithelium.

The galectin-3 immunoreactivity in corneal epithelium was similar when corneas were allowed to heal in serumfree Eagle's minimum essential medium containing nonessential amino acids, L-glutamine, antibiotics and 0.4% bovine serum albumin (BSA) in organ culture for 16 to 18 hours. However, anterior stroma of corneas that were allowed to heal in vitro lacked cells expressing galectin-3, suggesting that the galectin-3 positive cells seen in the stroma of corneas that were allowed to heal in vivo are most likely leukocytes and not keratocytes.

Figure 10:
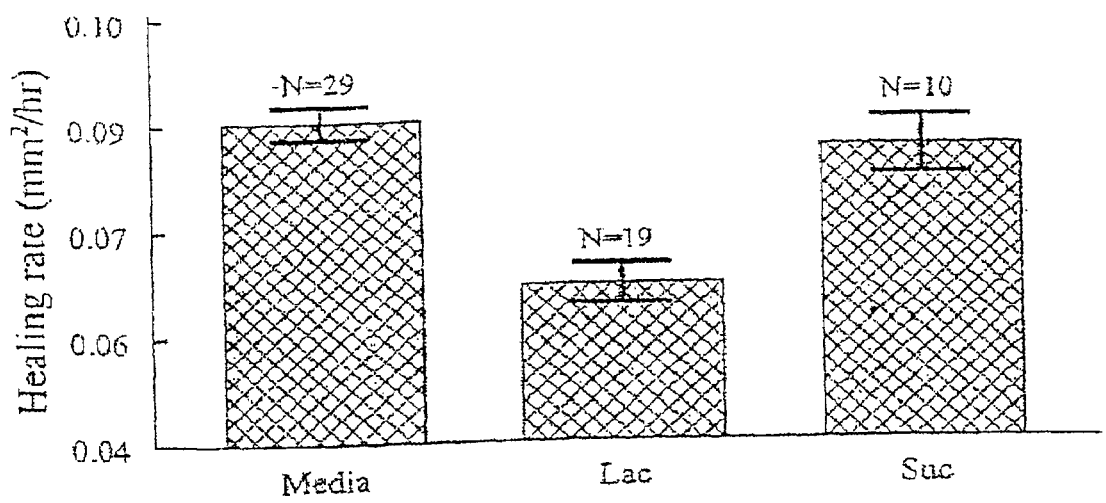
FIG. 10 is a graph illustrating the effect of β-lactose (Lac) and sucrose (Suc) on the healing rate of injured corneal epithelium.

To determine whether the carbohydrate recognition domain of galectin-3 plays a role in corneal epithelial sheet migration following injury, corneas with 2 mm excimer laser and abrasion wounds were allowed to heal in organ culture in the presence and absence of the disaccharides β-lactose and sucrose. While β-lactose contains galactose and binds galectins, sucrose lacks galactose and does not bind galectins. In these experiments, the rate of re-epithelialization of corneal wounds was significantly slower in the presence of β-lactose, while sucrose had no effect. As shown in FIG. 10, healing rates expressed as $mm^2/h$ among the different groups (mean±SEM of at least two experiments) were: media alone, 0.088±0.003 (N=29); media plus β-lactose, 0.063±0.003 (N=19); media plus sucrose 0.084±0.004 (N=10).

Example 2

Corneal Epithelial Wound Closure in Wild Type and Galectin-3 Deficient Mice

To determine whether the re-epithelialization of corneal wounds is impaired in galectin-3 deficient mice, four different models of corneal wound healing were used. Galectin-3 deficient mice (gal-$3^{-/-}$) were generated by targeted interruption of the galectin-3 gene as described in Hsu et al., *Am. J. Pathol.* 156:1073, 2000. Specifically, the region coding for the CRD was interrupted with a neomycin resistant gene. This involved substituting a 0.5 kb intron 4-exon 5 segment with the antibiotic resistant gene (neo). That the galectin-3 gene has been inactivated was confirmed by Southern blot as well as Western blot analysis.

Figure 11:
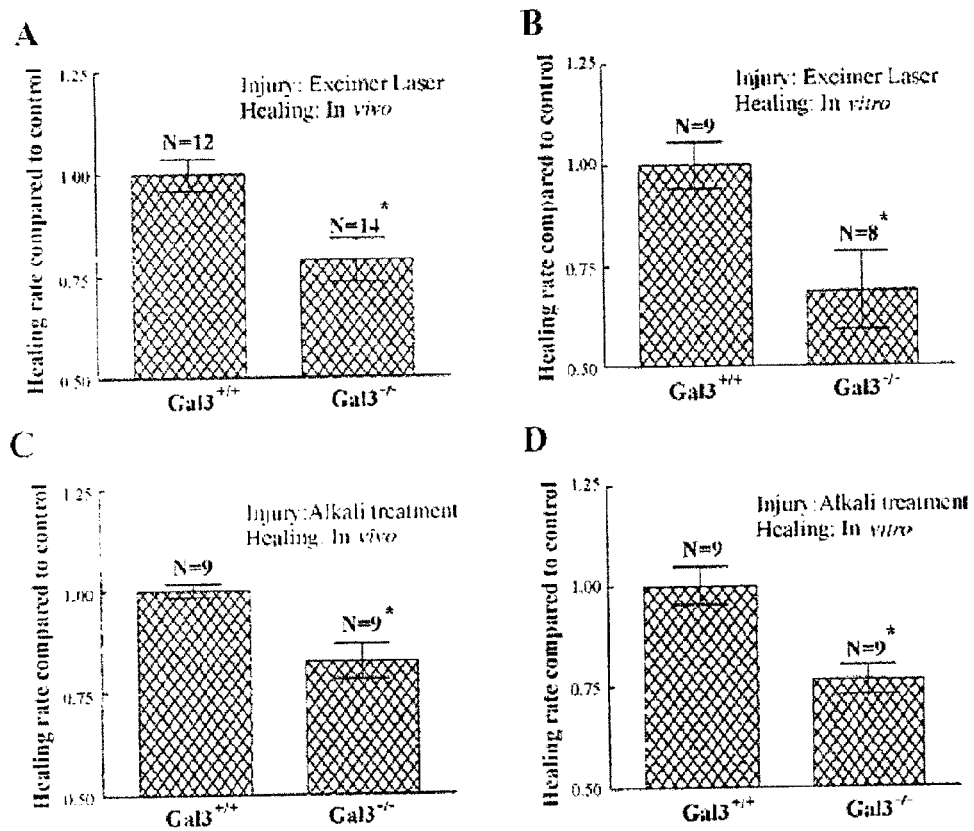
FIG. 11 is a series of graphs illustrating the healing rate of injured corneal epithelium in wild type (gal-3$^{+/+}$) and galectin-3 deficient (gal-3$^{-/-}$) mice injured by excimer laser or alkali treatment and allowed to heal in vivo or in vitro.

Briefly, corneas with excimer laser ablations (as described in Example 1) or alkali-burn wounds were allowed to partially heal in vivo or in vitro (as described in Example 1). For alkali injury, 2 mm filter discs (Whatman 50, Whatman International, Maidstone, UK) were prepared using a trephine, soaked in 0.5N NaOH, and placed on the surface of the cornea of the right eyes of a second group of mice for 30 seconds. The eyes were then rinsed with excess PBS. At the end of the healing period, the wound areas were visualized by staining with methylene blue. The stained wounds were then photographed at a standard distance, and the outlines of the wound areas were traced on paper from projected images of the stained wounds. These outlines were digitized and quantified using SIGMASCAN™ software (SPSS Science of Chicago, Ill.). Analysis of the wound closure rate in gal-$3^{+/+}$ mice in different models of wound healing revealed that wound closure rate expressed as $mm^2/h$ in gal-$3^{+/+}$ mice was slower in corneas injured with an excimer laser compared to those injured with an alkaliburn. Also, regardless of the injury method used, the wound closure rate was faster in corneas allowed to heal in vivo compared to those in organ culture. As shown in FIG. 11, wound closure rates among gal-$3^{+/+}$ groups were: 0.076±0.003 $mm^2/h$ for the excimer laser/in vivo group, 0.050±0.003 $mm^2/h$ for the excimer laser/in vitro group, 0.182±0.003 $mm^2/h$ for the alkali-burn/in vivo group, and 0.106±0.005 $mm^2/h$ for the alkali-burn/in vitro group. Each group represents the mean±SEM of at least two experiments (N=9 or more in each group). Comparison of the wound closure rate of gal-$3^{+/+}$ groups with gal-$3^{-/-}$ groups revealed that regardless of whether the corneas were injured by excimer laser or by alkali treatment and whether the corneas were allowed to heal in vivo or in vitro, corneal epithelial wound closure rate expressed in $mm^2/h$ was significantly slower in the gal-$3^{-/-}$ mice compared to that in the gal-$3^{+/+}$ mice. Wound closure rates among different gal-$3^{-/-}$ groups were 0.060±0.004 $mm^2/h$ for the excimer laser/in vivo group, 0.036±0.005 $mm^2/h$ for the excimer laser/in vitro group, 0.150±0.008 $mm^2$ for the alkali-burn/in vivo group, and 0.081±0.004 $mm^2/h$ for the alkali-burn/in vitro group. Again, all values are the mean±SEM of at least two experiments (N=8 or more in each group).

Example 3

Gene Expression Patterns in Migrating Corneal Epithelium of Galectin-3 Deficient Mice Following Injury In an attempt to understand why the re-epithelialization of corneal epithelial wounds is perturbed in gal-$3^{-/-}$ mice, gene expression patterns of healing gal-$3^{+/+}$ and gal-$3^{-/-}$ corneas were compared using cDNA microarrays and the results were further confirmed by semiquantitative RT-PCR.

Transepithelial excimer laser ablations (2 mm diameter) were produced on the right eye of 30 gal$^{+/+}$ and 30 gal$^{-/-}$ mice as described in Example 1. Corneas were allowed to partially heal in vivo for 20 to 24 hours. At the end of the healing period, animals were sacrificed and the corneas were excised and immediately placed in liquid nitrogen and shipped to Clontech Laboratories, Palo Alto, Calif. for analysis of gene expression using SMART™ cDNA technology. Briefly, total RNA was isolated using the reagents provided in the ATLAS™ Pure Total RNA Labeling System. Yield of RNA from the 30 gal-$3^{+/+}$ and 30 gal-$3^{-/-}$ corneas was 3.5 μg and 2.6 μg respectively. The A260:A280 ratio of the RNA preparations of the corneas of gal-3$^{+/+}$ and gal-3$^{-/-}$ mice were 1.48 and 1.37 respectively. The ribosomal RNA 28S:18S ratio was 1.8 for both preparations. This ensured that the quality of RNA preparation was satisfactory. For probe preparation, first strand cDNA was synthesized using 175 ng of RNA, a modified oligo(dT) primer (the CDS primer), POWERSCRIPT™ reverse transcriptase, and SMART™ II oligonucleotides. Controls involved incubation of samples without reverse transcriptase.

The cDNA was amplified by long distance (LD)-PCR. To determine the optimal number of amplification cycles, aliquots of reaction products were collected at 15, 18, 21 and 24 cycles and were analyzed by agarose gel electrophoresis. The yield of amplified double stranded cDNA using an optimal number of cycles, i.e., 23, was between 1 and 1.6 μg.

The amplified cDNAs (500 ng) were radiolabeled using Klenow enzyme and $^{33}$P-αATP as described in the instruction manual for SMART™ cDNA probe synthesis for ATLAS™ microarrays (Clontech). The labeled probes were purified by filtration on a NUCLEOSPIN™ filter and were then hybridized to mouse 1.2 k-I ATLAS™ nylon cDNA microarrays (Clontech). This is a broad spectrum array consisting of ~1200 mouse genes. Following hybridization, the membranes were exposed to a phosphorimager screen and the results were analyzed by ATLAS IMAGE™ 2.0 software (Clontech). The data were verified by semiquantitative RT-PCR.

Figure 12:
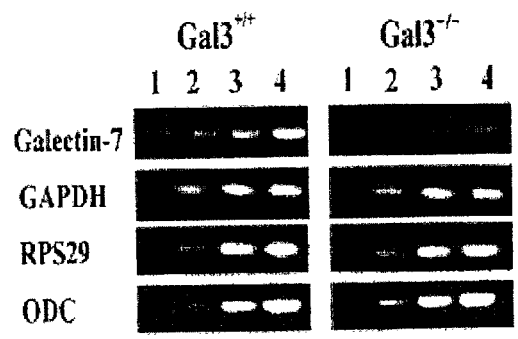
FIG. 12 is a table depicting differences in gene expression of galectin-7 and a selection of house keeping genes (GAPDH is D-glyceraldehyde-3-phosphate dehydrogenase; RPS29 is ribosomal protein S29; ODC is ornithine decarboxylase) between wild type (gal-3$^{+/+}$) and galectin-3 deficient (gal-3$^{-/-}$) mice as determined by cDNA microarray and semi-quantitative PCR.

For RT-PCR, total RNA and first strand cDNA were prepared from healing gal-3$^{+/+}$ and gal-3$^{-/-}$ corneas using the procedures described earlier. PCR amplification was performed in 50 μl volume using 14 ng of cDNA, gene-specific custom primers purchased from Clontech and other reagents from the ADVANTAGE™ 2 PCR kit (Clontech). The annealing temperature used was 68° C. and reactions were subjected to varying number of cycles of PCR amplification. For analysis of housekeeping genes, 5 μl aliquots of amplified product were collected at every 5$^{th}$ cycle, beginning at the 18$^{th}$ cycle, whereas for analysis of differentially expressed genes reaction amplified products were collected at every other cycle, beginning at the 28$^{th}$ cycle. Amplified products collected at various cycles were analyzed by electrophoresis in 1.5% agarose/ethedium bromide gels (FIG. 12).

These experiments revealed that compared to healing corneas of gal-3$^{+/+}$ mice, healing corneas of gal-3$^{-/-}$ mice contain markedly reduced levels of mRNA transcripts for galectin-7, another galactose-binding protein, and tolloid-like protein (TLL), a metalloproteinase. Overall, compared to healing gal-3$^{+/+}$ corneas, healing gal-3$^{-/-}$ corneas contained about 12 times less galectin-7 (FIG. 12) and 14 times less TLL gene transcripts (data not shown). Expression levels of mRNA transcripts of various housekeeping genes were similar in both healing gal-3$^{+/+}$ and gal-3$^{-/-}$ as detected by both microarray technology (FIG. 12), and semi-quantitative RT-PCR (FIG. 12, GAPDH is D-glyceraldehyde-3-phosphate dehydrogenase; RPS29 is ribosomal protein S29; ODC is ornithine decarboxylase).

Figure 13:
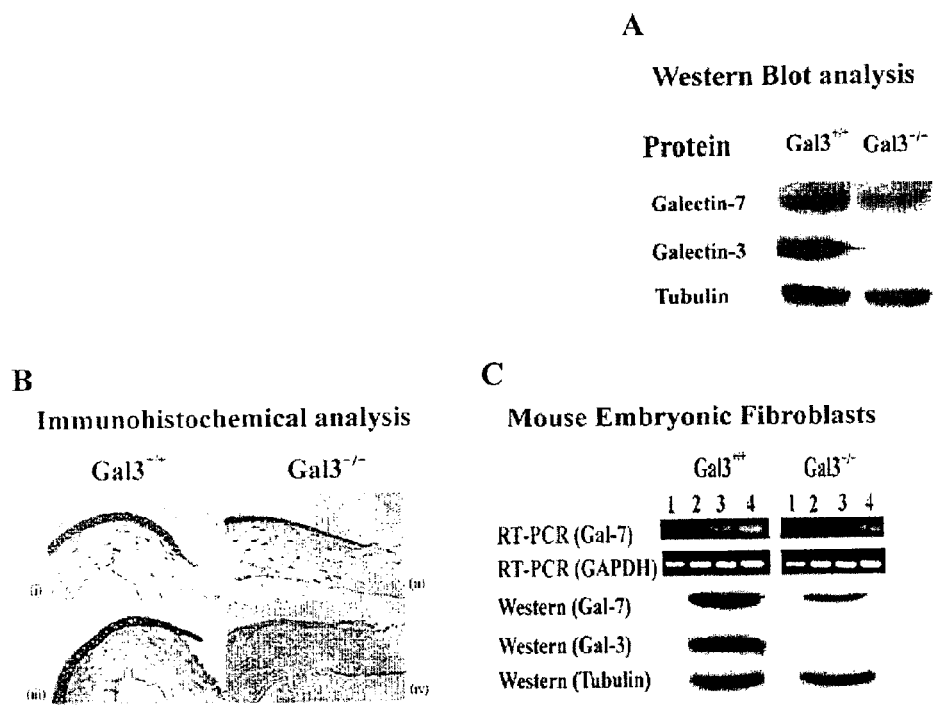
FIG. 13 illustrates differences in the expression of galectin-7 between wild type (gal-3$^{+/+}$) and galectin-3 deficient (gal-3$^{-/-}$) mice as determined by (A) western blot analysis, (B) immunohistochemical analysis, and (C) using mouse embryonic fibroblasts.

To determine whether the expression level of the galectin-7 protein is also reduced in healing corneas of gal-3$^{-/-}$ mice, western blot analysis using detergent extracts of healing gal-3$^{+/+}$ and gal-3$^{-/-}$ corneas (FIG. 13A) and immunohistochemical studies with an anti-galectin-7 polyclonal antibody using paraffin sections derived from corneas of gal-3$^{+/+}$ and gal-3$^{-/-}$ mice (FIG. 13B) were performed. The immunoreactivity was graded as intense (+++), moderate (++), weak (+) or negative (–). Significantly less galectin-7 immunoreactivity was detected in migrating epithelia of healing gal-3$^{-/-}$ corneas compared to those of healing gal-3$^{+/+}$ corneas: gal-3$^{+/+}$:+++36/42, ++5/42, + or less 1/42; gal-3$^{-/-}$:+++3/42, ++26/42, + or less 13/42. Also, gal-3$^{-/-}$ mouse embryonic fibroblasts (MEF) grown in cell culture expressed reduced levels of galectin-7 compared to gal-3$^{+/+}$ MEF cultures (FIG. 13C).

Example 4

Exogenous Galectin-3 Stimulates the Re-epithelialization of Corneal Wounds in Wild Type and Galectin-3 Deficient Mice Having demonstrated that corneal epithelial wound closure rate is perturbed in gal-3$^{-/-}$ mice (Example 2), it was of interest to determine whether exogenous galectin-3 would stimulate the re-epithelialization of healing corneas in organ culture. In this study, corneas of gal-3$^{+/+}$ and gal-3$^{-/-}$ mice with alkali-burn wounds were incubated in serum free media in the presence and absence of varying amounts of recombinant galectin-3.

Recombinant full-length human galectin-3 was produced in *Eschericia coli* and purified as described previously (Yang et al., *Biochemistry* 37:4086, 1998). Alkali-burn wounds (2 mm diameter) were produced on both eyes of anesthetized mice using alkali-soaked filter discs as described in Example 2. Following injury, the animals were sacrificed and the eyes were excised and incubated in the presence or absence of exogenous galectin-3 for 18 to 20 hours. The left eyes of animals served as controls and were incubated in serum free media alone. The right eyes were incubated in serum free media containing various test reagents including: (i) galectin-3 (5 to 20 μg/ml), (ii) galectin-3 (10 μg/ml) plus 0.1 M β-lactose, (iii) galectin-3 (10 μg/ml) plus 0.1 M sucrose, (iv) 0.1 M β-lactose, or (v) 0.1 M sucrose. At the end of the healing period, the remaining wound areas were stained, photographed and quantified as described in Example 2 using SIGMASCAN™ software (SPSS Science of Chicago, Ill.). Each group contained a minimum of three eyes and all experiments were performed at least twice.

Figure 15:
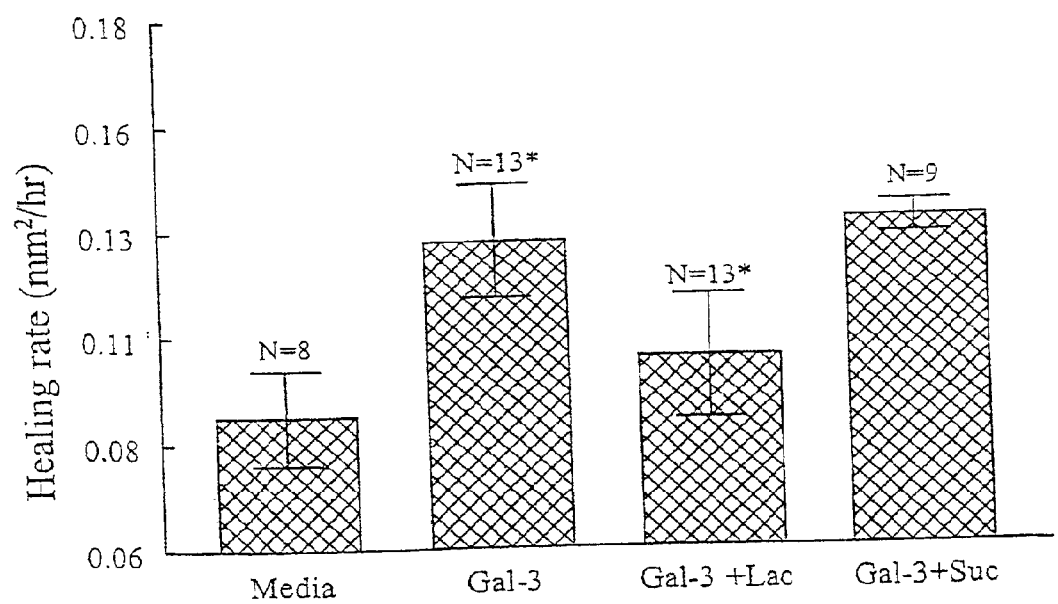
FIG. 15 is a graph illustrating the effect of β-lactose (Lac) and sucrose (Suc) on the healing rate of injured corneal epithelium of wild type (gal-3$^{+/+}$) mice in the presence of exogenous galectin-3.

The exogenous galectin-3 had no influence on the rate of re-epithelialization of corneal wounds in gal-3$^{-/-}$ mice (FIG. 14A), but it stimulated the rate of wound closure in a concentration-dependent manner in gal-3$^{+/+}$ mice (FIG. 14B) at 10 μg/ml and 20 μg/ml concentration (0 and 5 μg/ml: 0.090±0.010 mm$^2$/h; 10 μg/ml: 0.129±0.010 mm$^2$/h; 20 μg/ml: 0.154±0.004 mm$^2$/h; mean±SEM of at least two experiments, N=7 or more). As shown in FIG. 15, the stimulatory effect of galectin-3 on corneal epithelial wound closure in gal-3$^{+/+}$ mice was specifically inhibited by β-lactose but not sucrose (10 μg/ml galectin-3: 0.127±0.010 mm$^2$/h; 10 μg/ml galectin-3 plus 0.1 M β-lactose: 0.103±0.014 mm$^2$/h; 10 μg/ml galectin-3 plus 0.1 M sucrose: 0.130±0.003 mm$^2$/h. All values represent mean±SEM of at least two experiments, N=7 or more).

Example 5

Exogenous Galectin-7 Stimulates the Re-epithelialization of Corneal Wounds in Wild Type and Galectin-3 Deficient Mice In a separate study, comparison of the gene expression patterns of normal and healing corneas of gal-3$^{+/+}$ mice using cDNA microarrays (i.e., as in Example 3) revealed that in healing corneas, expression of galectin-7 is markedly up-regulated. These findings in conjunction with the studies described in Example 3 showing that galectin-7 expression is down-regulated in the healing cornea of gal-3$^{-/-}$ mice, led to the design of experiments to determine whether exogenous galectin-7 would stimulate the re-epithelialization of healing corneas in organ culture. In this study, corneas of gal-3$^{-/-}$ mice with alkali-burn wounds were incubated in serum free media in the presence and absence of varying amounts of recombinant galectin-7.

Recombinant full-length human galectin-7 was produced in *Eschericia coli* by cloning the cDNA (available as an EST clone from American Type Culture Collection of Manassas, Va.) into the pET25b plasmid (available from Novagen, Madison, Wis.). Alkali-burn wounds (2 mm diameter) were produced on both eyes of anesthetized animals using alkali-soaked filter discs as described in Example 2. Following injury, the animals were sacrificed and the eyes were excised and incubated in the presence or absence of exogenous galectin-7 for 18 to 20 hours. The left eyes of animals served as controls and were incubated in serum free media alone. The right eyes were incubated in serum free media containing various test reagents including: (i) galectin-7 (20 µg/ml), (ii) galectin-7 (20 µg/ml) plus 0.1 M β-lactose, or (iii) galectin-7 (20 µg/ml) plus 0.1 M sucrose. At the end of the healing period, the remaining wound areas were stained, photographed and quantified as described in Example 2 using SIGMASCAN™ software (SPSS Science of Chicago, Ill.). Each group contained a minimum of six eyes and all experiments were performed at least twice.

As shown in FIG. 16, exogenous galectin-7 stimulated the rate of wound closure (media alone: 0.036±0.006 mm$^2$/h; 20 µg/ml galectin-7: 0.072±0.004 mm$^2$/h; mean±SEM of at least two experiments, N=10 or more). As shown in FIG. 16, the stimulatory effect of galectin-7 on corneal epithelial wound closure was specifically inhibited by β-lactose but not by sucrose (20 µg/ml galectin-7: 0.072±0.004 mm$^2$/h; 20 µg/ml galectin-7 plus 0.1 M β-lactose: 0.050±0.004 mm$^2$/h; 20 µg/ml galectin-7 plus 0.1 M sucrose: 0.079±0.007 mm$^2$/h. All values represent mean±SEM of at least two experiments, N=9 or more). As shown in FIG. 16, the rate of wound closure was further enhanced (0.094±0.003 gal-3$^{+/+}$ mm$^2$/h) when exogenous galectin-7 was added to the injured corneas of gal-3$^{+/+}$ mice instead of gal-3$^{-/-}$ mice.

Example 6

Skin Epithelial Wound Closure in Wild Type and Galectin-3 Deficient Mice

Gal-3$^{+/+}$ and gal-3$^{-/-}$ mice are anesthetized by an intraperitoneal injection of 1.25% Avertin (0.2 ml/10 g body weight). Prior to laser treatment, hair is shaved off from the dorsal region using a razor blade. Six millimeter transepithelial dorsal skin wounds are made using the excimer laser (Summit Technology of Waltham, Mass.). After surgery, antibiotic ointment is applied to the wound surface and buprenorphine (2 mg/kg body weight) is given subcutaneously to minimize post-surgical pain. The wounds are allowed to partially heal in vivo, and are examined 24, 48, and 72 hours after surgery. At the end of the healing period, the mice are again anesthetized by an intraperitoneal injection of 1.25% Avertin (0.2 ml/10 g body weight), wound areas are photographed and then quantitated using a Sigma scan software. The wound closure rates between the two groups of animals (i.e., gal-3$^{+/+}$ and gal-3$^{-/-}$ mice) are compared. The animals are then sacrificed by carbon dioxide inhalation or an overdose of pentobarbital.

Example 7

Effect of Exogenous Galectin-3 on the the Re-epithelialization of Skin Wounds

Animals (Mice: 57BL/6 and 129 mixed genetic background; Age: six to eight weeks old; Gender: mixed) are anesthetized by an intraperitoneal injection of 1.25% Avertin (0.2 ml/10 g body weight). Prior to laser treatment, hair is shaved off from the dorsal region using a razor blade. Two 6-mm transepithelial dorsal skin wounds (one on each side) are made using the excimer laser (Summit Technology of Waltham, Mass.). After surgery, antibiotic ointment is applied to the wound surfaces and buprenorphine (2 mg/kg body weight) is given subcutaneously to minimize post-surgical pain. The wounds are then allowed to partially heal in vivo. Every 4–6 hours, an ointment containing galectin-3 is applied to the right wound and carrier only is applied to the left wound which serves as a control. At the end of the healing period (24 to 48 hours), the animals are anesthetized by an intraperitoneal injection of 1.25% Avertin (0.2 ml/10 g body weight), wound areas are photographed and quantitated using a Sigma scan software. The wound closure rates between the two groups of animals (galectin-3 treated and control) are compared. The animals are then sacrificed by carbon dioxide inhalation or an overdose of pentobarbital.

Example 8

Effect of Exogenous Galectin-7 on the the Re-epithelialization of Skin Wounds

Animals (Mice: 57BL/6 and 129 mixed genetic background; Age: six to eight weeks old; Gender: mixed) are anesthetized by an intraperitoneal injection of 1.25% Avertin (0.2 ml/10 g body weight). Prior to laser treatment, hair is shaved off from the dorsal region using a razor blade. Two 6-mm transepithelial dorsal skin wounds (one on each side) are made using the excimer laser (Summit Technology of Waltham, Mass.). After surgery, antibiotic ointment is applied to the wound surfaces and buprenorphine (2 mg/kg body weight) is given subcutaneously to minimize post-surgical pain. The wounds are then allowed to partially heal in vivo. Every 4–6 hours, an ointment containing galectin-7 is applied to the right wound and carrier only is applied to the left wound which serves as a control. At the end of the healing period (24 to 48 hours), the animals are anesthetized by an intraperitoneal injection of 1.25% Avertin (0.2 ml/10 g body weight), wound areas are photographed and quantitated using a Sigma scan software. The wound closure rates between the two groups of animals (galectin-7 treated and control) are compared. The animals are then sacrificed by carbon dioxide inhalation or an overdose of pentobarbital.

Conclusion

It has been demonstrated that galectin-3 and galectin-7 play a role in the re-epithelialization of corneal wounds. In Example 1 immunohistochemical studies revealed that following injury, galectin-3 is located in high density at sites of corneal epithelial cell-matrix adhesion, an ideal location for influencing cell-matrix interactions and hence cell migration. In Example 2, the re-epithelialization of corneal wounds was shown to be significantly slower in the galectin-3 deficient mice compared to that in wild-type mice. In Example 3, it was shown that following injury, expression levels of galectin-7 are significantly reduced in galectin-3 deficient mice compared to wild-type mice. In Examples 4 and 5, exogenous recombinant galectin-3 and galectin-7 were shown to stimulate the re-epithelialization of corneal wounds in gal3$^{+/+}$ mice. It was further demonstrated in Example 1 that the stimulatory effect of galectin-3 on the rate of corneal epithelial wound closure can be almost completely abrogated by a competing disaccharide (β-lactose), but not by an irrelevant disaccharide (sucrose). This final result suggests that the carbohydrate recognition domain (CRD) is directly involved in the beneficial effect of the exogenous galectin-3 on wound closure.

Without wishing to be bound to any particular theory regarding the mechanism by which galectin-3 and galectin-7 may influence re-epithelialization of corneal wounds, the following suggestions are presented.

As mentioned earlier, galectin-3 is thought to mediate cell-cell and cell-matrix interactions by binding to complementary glycoconjugates containing polylactosamine chains found in many ECM and cell surface molecules such as certain isoforms of fibronectin, laminin, and integrins (Liu, *Clin. Immunol.* 97:79, 2000 and Perillo, supra). However, the finding presented herein that exogenous galectin-3 does not accelerate the re-epithelialization of wounds in gal3$^{-/-}$ mice (see Example 4) suggests that intracellular galectin-3 contributes significantly to the process of wound healing, most probably, by influencing the expression of specific cell surface and/or ECM receptors, which in turn influence cell-matrix interactions and cell migration. This idea is consistent with published studies in which galectin-3 was stably overexpressed in breast carcinoma cell lines, resulting in elevated levels of α4β7 and α6β1 integrins and enhanced adhesion to various ECM molecules including laminin, fibronectin, and vitronectin as compared with parental cell lines expressing little or no galectin-3 (Warfield, supra and Mattarese, supra). In another study (Dudas et al., *Gastroenterology* 118:1553, 2000), colon cancer carcinoma cell lines transfected with galectin-3 expressed elevated levels of a specific mucin, MUC2, a major ligand of the lectin itself (Bresalier et al., *Cancer Research* 56:4354, 1996). The fact that the stimulatory effect of exogenous galectin-3 on the rate of re-epithelialization of wounds in gal3$^{+/+}$ mice is lactose inhibitable raises an intriguing possibility that intracellular galectin-3 may in fact regulate glycosylation of the proteins which serve as cell surface or ECM receptors of the lectin itself. That intracellular galectin-3 has the potential to act on the nuclear matrix to influence complex biological processes is also suggested by findings that under certain conditions the lectin can be found associated in the nucleus with ribonucleoprotein complexes and can act as a pre-mRNA splicing factor (Dagher et al., *Proc. Natl. Acad. Sci. USA* 92:1213, 1995). Also, Wang et al. have demonstrated that in prostate adenocarcinoma cells, galectin-3 is associated with the nuclear matrix and binds with both single-stranded DNA and RNA (Wang et al., *Biochem. Biophys. Res. Commun.* 217:292, 1995).

Analysis of gene expression patterns of corneas of healing gal3$^{+/+}$ and gal3$^{-/-}$ mice using mouse cDNA microarrays revealed that healing corneas of gal3$^{-/-}$ mice expressed markedly reduced levels of galectin-7 compared to those of wild-type mice (see Examples 3 and 5). Galectin-7 was first reported in 1994 (Barondes, supra) and is not as well characterized as galectin-3. Unlike galectin-3, galectin-7 exhibits a remarkable degree of tissue specificity. In adult animals, its expression is restricted to epithelia that are or are destined to become stratified (Timmons et al., supra). The protein is thought to be involved in cell-matrix and cell-cell interactions and in apoptosis (Leonidas, *Biochemistry* 37:13930, 1998 and Bernerd et al., *Proc. Natl. Acad. Sci. USA* 96:11329, 1999). In general, an inverse correlation exists between galectin-7 expression and keratinocyte proliferation, and galectin-7 expression is abrogated in SV40 transformed keratinocytes as well as in cell lines derived from epidermal tumors. The discovery described herein that exogenous galectin-3 does not stimulate re-epithelialization of wounds in gal3$^{-/-}$ corneas and that healing gal3$^{-/-}$ corneas contain reduced levels of galectin-7 suggests that galectin-3 may influence the re-epithelialization of wounds, at least in part, by modulating galectin-7. Indeed, it has been found that unlike galectin-3, galectin-7 accelerated re-epithelialization of wounds in gal3$^{-/-}$ corneas in a lactose-inhibitable manner. Also, mouse embryonic fibroblasts of gal3$^{-/-}$ mice expressed reduced level of galectin-7.

Regardless of the mechanisms involved, the findings that both galectin-3 and galectin-7 stimulate re-epithelialization of corneal wounds have broad implications for the treatment of epithelial wounds and non-healing epithelial wounds in particular. At present, treatment of persistent epithelial defects of the cornea is a major clinical problem. Moreover, the need continues for effective treatment of post-transplantation wounds, chronic wounds in the elderly, decubitus ulcers, and venous stasis ulcers of the skin. A number of growth factors (e.g., EGF, TGF, FGF, KGF, HGF) known to stimulate cell proliferation, have been tested for usefulness in corneal as well as cutaneous epithelial wound healing with overall disappointing results (Eaglstein, *Surg. Clin. North Am.* 77:689, 1997; Singer and Clark, *N. Engl. J. Med.* 341:738, 1999; Zieske and Gipson, pp. 364–372 in "Principle and Practice of Ophthalmology" Ed. by D. M. Albert and F. A. Jakobiec, W. B. Saunders Company, Philadelphia, Pa., 2000; Schultz et al., *Eye* 8:184, 1994; Kandarakiset al., *Am. J. Ophthalmol.* 98:411, 1984; and Singh and Foster, *Am. J. Ophthalmol.* 103:802, 1987). The extent of acceleration of re-epithelialization of wounds was far less in most of these studies using growth factors than that observed with galectins in the current study. Also, the epithelium of corneas treated with growth factors such as EGF is hyperplastic (Singh and Foster, *Cornea* 8:45, 1989), a clearly undesirable condition. In this respect, the clinical potential of galectin-3 and galectin-7 may be more attractive than that of growth factors because the lectins have not been shown to induce cell mitosis in epithelial cells. Over the last decade, the potential of excimer laser keratectomy to modify the corneal profile for correction of myopia has been realized. Thousands of such procedures are performed each week providing myopic individuals freedom from eye glasses and contact lenses. In view of the fact that 25–30% of the adult population worldwide is myopic, it has been estimated that nearly half a million such procedures will be performed in the U.S. alone in a given year. In some cases, following excimer laser surgery, there is a delay in epithelial healing. Such a delay is highly undesirable because it puts the cornea at risk of developing postoperative haze, infectious keratitis and ulceration. Again, galectin-based treatments may help promote re-epithelialization of wounds in such cases.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:

1. A method for the therapeutic treatment of corneal wounds in mammals comprising administering to a mammal afflicted with a corneal wound a therapeutically effective amount of a galectin-3 protein, the protein having a galectin-3 N-terminal domain, a galectin-3 proline, glycine, and tyrosine-rich domain, and a galectin-3 galactoside-binding domain.

2. The method according to claim 1, wherein said corneal wound is a lesion or an erosion.

3. The method according to claim 1, wherein said corneal wound is a persistent corneal defect or a recurrent corneal erosion.

4. The method according to claim 1, wherein said corneal wound was caused by excimer laser keratectomy.

5. The method of claim 1, wherein the galectin-3 protein comprises the amino acid sequence of SEQ ID NO:1.

6. A method for the therapeutic treatment of corneal wounds in mammals comprising administering to a mammal afflicted with an corneal wound a therapeutically effective amount of a galectin-3 protein that influences the expression of corneal cell surface receptors or receptors of the corneal extracellular matrix, wherein the galectin-3 protein comprises an amino acid sequence having at least 80% identity with the amino acid sequence of SEQ ID NO:1.

7. The method of claim 6, galectin-3 protien is identical to the amino acid sequence of SEQ ID NO: 1.

8. The method of claim 6, wherein said galectin-3 protein comprises an N-terminal domain of about 14 amino acids in length and has an amino acid sequence having at least 80% identity with amino acids at positions 1 to 14 of SEQ ID NO:1.

9. The method of claim 6, wherein said galectin-3 protein comprises a proline, glycine, and tyrosine-rich domain of about 90 to 110 amino acids in length, and shares at least 80% identity with amino acids at positions 15 to 116 of SEQ ID NO:1.

10. The method of claim 6, wherein said galectin-3 protein comprises a galactose-binding domain of 120 to 140 amino acids in length and has a galaptin signature sequence as shown in SEQ ID NO: 28, and the galectin-3 galactoside-binding domain includes the following amino acids and regions of SEQ ID NO:1: P117, Y118, L120–L122, G125, P128, R129, L131–I134, G136–V138, N141, N143, R144, L147, F149, R151, G152, D154, A156–F163, E165, R169–N174, N179–G182, E184–R186, F190–E193, G195, P197–K199, Q201–L203, E205, D207–Q220, N222, R224, L228, I231, I236, G238–I240, and L242–S244.

11. A method for therapeutically treating a corneal pathology, the method comprising administering to a subject afflicted with the corneal pathology a therapeutically effective amount of a pharmaceutical composition comprising a galectin-3 protein.

12. The method of claim 11, wherein said pathology is at least one corneal condition or associated with at least one corneal injury selected from the group consisting of: keratities, corneal ulcers, heat burns, chemical burns, radiation burns, phlyctenulosis, corneal abrasions, corneal lacerations, surgery, foreign bodies, corneal cuts, corneal infiltrates and corneal dystrophies.

13. The method of claim 12, wherein said corneal pathology is persistent, recurrent, or chronic.

14. The method of claim 11, wherein said subject is a mammal.

15. The method of claim 11, wherein said subject is a human.

16. The method of claim 11, wherein said subject is selected from the group of bovine, canine, feline, caprine, ovine, porcine, murine, lagomorph, and equine species.

17. The method of claim 12, wherein said keratities is a bacterial keratitis or a viral keratitis.

18. The method of claim 17, wherein said viral keratitis is metaherpetic or herpetic.

19. The method of claim 12, wherein said dystrophies are selected from the group consisting of at least one of lattice dystrophy, epithelial basement membrane dystrophy, and Fuch's endothelial dystrophy.

20. A method for the therapeutic treatment of corneal wounds in mammals comprising administering to a mammal afflicted with an corneal wound a therapeutically effective amount of galectin-3 as shown in SEQ ID NO: 1.

* * * * *

UNITED STATES PATENT AND TRADEMARK OFFICE
CERTIFICATE OF CORRECTION

PATENT NO. : 6,967,021 B2  Page 1 of 1
APPLICATION NO. : 10/133234
DATED : November 22, 2005
INVENTOR(S) : Panjwani et al.

It is certified that error appears in the above-identified patent and that said Letters Patent is hereby corrected as shown below:

On column 1, lines 13-14, delete "Accordingly, the government may have certain rights in this invention."

and insert --Accordingly, the government has certain rights in the invention.--

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 6,967,021 B2  Page 1 of 1
APPLICATION NO. : 10/133234
DATED : November 22, 2005
INVENTOR(S) : Panjwani et al.

It is certified that error appears in the above-identified patent and that said Letters Patent is hereby corrected as shown below:

On column 1, lines 11-14, delete "This invention was made with Government support under grant number EY-07088 from the National Institutes of Health. Accordingly, the government has certain rights in this invention."

and insert --This invention was made with government support under EY07088 awarded by the National Institutes of Health. The government has certain rights in the invention.--

This certificate supersedes the Certificate of Correction issued June 1, 2010.

Signed and Sealed this
Ninth Day of October, 2012

David J. Kappos
*Director of the United States Patent and Trademark Office*

SEQUENCE LISTING

<160> NUMBER OF SEQ ID NOS: 28

<210> SEQ ID NO 1
<211> LENGTH: 250
<212> TYPE: PRT
<213> ORGANISM: Human

<400> SEQUENCE: 1

Met Ala Asp Asn Phe Ser Leu His Asp Ala Leu Ser Gly Ser Gly Asn
 1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr His
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 2
<211> LENGTH: 136
<212> TYPE: PRT
<213> ORGANISM: Human

<400> SEQUENCE: 2

Met Ser Asn Val Pro His Lys Ser Ser Leu Pro Glu Gly Ile Arg Pro
 1               5                   10                  15

Gly Thr Val Leu Arg Ile Arg Gly Leu Val Pro Pro Asn Ala Ser Arg
            20                  25                  30

Phe His Val Asn Leu Leu Cys Gly Glu Glu Gln Gly Ser Asp Ala Ala
        35                  40                  45

Leu His Phe Asn Pro Arg Leu Asp Thr Ser Glu Val Val Phe Asn Ser
    50                  55                  60

```
Lys Glu Gln Gly Ser Trp Gly Arg Glu Arg Gly Pro Gly Val Pro
 65                  70                  75                  80

Phe Gln Arg Gly Gln Pro Phe Glu Val Leu Ile Ile Ala Ser Asp Asp
                 85                  90                  95

Gly Phe Lys Ala Val Val Gly Asp Ala Gln Tyr His His Phe Arg His
            100                 105                 110

Arg Leu Pro Leu Ala Arg Val Arg Leu Val Glu Val Gly Gly Asp Val
            115                 120                 125

Gln Leu Asp Ser Val Arg Ile Phe
    130                 135

<210> SEQ ID NO 3
<211> LENGTH: 139
<212> TYPE: PRT
<213> ORGANISM: Artificial Sequence
<220> FEATURE:
<223> OTHER INFORMATION: Description of Artificial Sequence:
      Galactoside-binding lectin domain, PF00337.

<400> SEQUENCE: 3

Pro Gly Leu Val Ala Leu Asn Leu Gly Leu Lys Pro Gly Lys Thr Leu
 1               5                  10                  15

Thr Val Lys Gly Thr Val Ala Pro Lys Asn Ala Lys Arg Phe Ala Val
                 20                  25                  30

Asn Leu Gly Lys Gly Ser Lys Glu Glu Asn Asp Leu Val Leu His Phe
            35                  40                  45

Asn Pro Arg Phe Asn Glu Ala His Gly Asp Gln Asn Thr Val Val Cys
    50                  55                  60

Asn Ser Lys Glu Asn Gly Asp Asn Glu Trp Gly Thr Glu Gln Arg Glu
 65                  70                  75                  80

Ala Ala Phe Pro Phe Gln Ala Gly Gln Pro Phe Glu Ile Ser Ile Ser
                 85                  90                  95

Val Glu Glu Asp Lys Phe Lys Val Lys Val Asn Asp Gly His Glu Phe
            100                 105                 110

Glu Phe Pro His Arg Leu Lys Leu Glu Ala Val Gln Tyr Leu Gly Ile
            115                 120                 125

Lys Gly Asp Ile Lys Leu Thr Ser Ile Lys Phe
    130                 135

<210> SEQ ID NO 4
<211> LENGTH: 242
<212> TYPE: PRT
<213> ORGANISM: Rabbit

<400> SEQUENCE: 4

Met Ala Asp Gly Phe Ser Leu Asn Asp Ala Leu Ser Gly Ser Gly His
 1               5                  10                  15

Pro Pro Asn Gln Gly Trp Pro Gly Pro Trp Gly Asn Gln Pro Ala Gly
                 20                  25                  30

Pro Gly Gly Tyr Pro Gly Ala Ala Tyr Pro Gly Ala Tyr Pro Gly His
            35                  40                  45

Ala Pro Gly Ala Tyr Pro Gly Gln Ala Pro Gly Pro Tyr Pro Gly
    50                  55                  60

Pro Gly Ala His Gly Ala Tyr Pro Gly Gln Pro Gly Pro Gly Ala
 65                  70                  75                  80

Tyr Pro Ser Pro Gly Gln Pro Ser Gly Ala Gly Ala Tyr Pro Gly Ala
                 85                  90                  95
```

```
Ser Pro Tyr Ser Ala Ser Ala Gly Pro Leu Pro Val Pro Tyr Asp Leu
            100                 105                 110

Pro Leu Pro Gly Gly Val Met Pro Arg Met Leu Ile Thr Ile Val Gly
        115                 120                 125

Thr Val Lys Pro Asn Ala Asn Arg Leu Ala Leu Asp Phe Lys Arg Gly
        130                 135                 140

Asn Asp Val Ala Phe His Phe Asn Pro Arg Phe Asn Glu Asn Asn Arg
145                 150                 155                 160

Arg Val Ile Val Cys Asn Thr Lys Val Asp Asn Asn Trp Gly Arg Glu
                165                 170                 175

Glu Arg Gln Thr Thr Phe Pro Phe Glu Ile Gly Lys Pro Phe Lys Ile
            180                 185                 190

Gln Val Leu Val Glu Pro Asp His Phe Lys Val Ala Val Asn Asp Ala
        195                 200                 205

His Leu Leu Gln Tyr Asn His Arg Met Arg Asn Leu Lys Glu Ile Asn
    210                 215                 220

Lys Leu Gly Ile Ser Gly Asp Ile Gln Leu Thr Ser Ala Ser His Ala
225                 230                 235                 240

Met Ile

<210> SEQ ID NO 5
<211> LENGTH: 262
<212> TYPE: PRT
<213> ORGANISM: Chicken

<400> SEQUENCE: 5

Met Gln Ala Met Lys Ala Arg Cys Trp Gln Pro His Trp Met Leu Pro
1               5                   10                  15

Leu Leu Pro Leu Ser Ser Pro Leu His Pro Gln Leu Ser Asp Ala Leu
            20                  25                  30

Pro Ala His Asn Pro Gly Ala Pro Pro Gln Gly Trp Asn Arg Pro
        35                  40                  45

Pro Gly Pro Gly Ala Phe Pro Ala Tyr Pro Gly Tyr Pro Gly Ala Tyr
    50                  55                  60

Pro Gly Ala Pro Gly Pro Tyr Pro Gly Ala Pro Gly Pro His His Gly
65                  70                  75                  80

Pro Pro Gly Pro Tyr Pro Gly Gly Pro Pro Gly Pro Tyr Pro Gly Gly
            85                  90                  95

Pro Pro Gly Pro Tyr Pro Gly Gly Pro Pro Gly Pro Tyr Pro Gly Gly
            100                 105                 110

Pro Thr Ala Pro Tyr Ser Glu Ala Pro Ala Ala Pro Leu Lys Val Pro
        115                 120                 125

Tyr Asp Leu Pro Leu Pro Ala Gly Leu Met Pro Arg Leu Leu Ile Thr
        130                 135                 140

Ile Thr Gly Thr Val Asn Ser Asn Pro Asn Arg Phe Ser Leu Asp Phe
145                 150                 155                 160

Lys Arg Gly Gln Asp Ile Ala Phe His Phe Asn Pro Arg Phe Lys Glu
                165                 170                 175

Asp His Lys Arg Val Ile Val Cys Asn Ser Met Phe Gln Asn Asn Trp
        180                 185                 190

Gly Lys Glu Glu Arg Thr Ala Pro Arg Phe Pro Phe Glu Pro Gly Thr
    195                 200                 205

Pro Phe Lys Leu Gln Val Leu Cys Glu Gly Asp His Phe Lys Val Ala
210                 215                 220
```

Val Asn Asp Ala His Leu Leu Gln Phe Asn Phe Arg Glu Lys Lys Leu
225                 230                 235                 240

Asn Gly Ile Thr Lys Leu Cys Ile Ala Gly Asp Ile Thr Leu Thr Ser
            245                 250                 255

Val Leu Thr Ser Met Ile
            260

<210> SEQ ID NO 6
<211> LENGTH: 245
<212> TYPE: PRT
<213> ORGANISM: Hamster

<400> SEQUENCE: 6

Met Ala Asp Gly Phe Ser Leu Asn Asp Ala Leu Ala Gly Ser Gly Asn
1               5                   10                  15

Pro Asn Pro Gln Gly Trp Pro Gly Ala Trp Gly Asn Gln Pro Gly Ala
            20                  25                  30

Gly Gly Tyr Pro Gly Ala Ser Tyr Pro Gly Ala Tyr Pro Gly Gln Ala
        35                  40                  45

Pro Pro Gly Ala Tyr Pro Gly Gln Ala Pro Pro Gly Ala Tyr Pro Gly
    50                  55                  60

Pro Thr Ala Pro Gly Ala Tyr Pro Gly Pro Ala Pro Gly Ala Tyr Pro
65                  70                  75                  80

Gly Gln Pro Gly Ala Ser Gly Ala Tyr Pro Ser Ala Pro Gly Ala Tyr
                85                  90                  95

Pro Ala Ala Gly Pro Tyr Gly Ala Pro Thr Gly Ala Leu Thr Val Pro
            100                 105                 110

Tyr Lys Leu Pro Leu Ala Gly Gly Val Met Pro Arg Met Leu Ile Thr
        115                 120                 125

Ile Met Gly Thr Val Lys Pro Asn Ala Asn Arg Ile Ile Leu Asn Phe
130                 135                 140

Leu Arg Gly Asn Asp Ile Ala Phe His Phe Asn Pro Arg Phe Asn Glu
145                 150                 155                 160

Asn Asn Arg Arg Val Ile Val Cys Asn Thr Lys Gln Asp Asn Asn Trp
                165                 170                 175

Gly Arg Glu Glu Arg Gln Ser Ala Phe Pro Phe Glu Ser Gly Arg Pro
            180                 185                 190

Phe Lys Ile Gln Val Leu Val Glu Ala Asp His Phe Lys Val Ala Val
        195                 200                 205

Asn Asp Ala His Leu Leu Gln Tyr Asn His Arg Met Lys Asn Leu Arg
210                 215                 220

Glu Ile Asn Gln Met Glu Ile Ser Gly Asp Ile Thr Leu Thr Ser Ala
225                 230                 235                 240

Ala Pro Thr Met Ile
            245

<210> SEQ ID NO 7
<211> LENGTH: 136
<212> TYPE: PRT
<213> ORGANISM: Rat

<400> SEQUENCE: 7

Met Ser Ala Thr His His Lys Thr Pro Leu Pro Gln Gly Val Arg Leu
1               5                   10                  15

Gly Thr Val Met Arg Ile Arg Gly Val Val Pro Asp Gln Ala Gly Arg
            20                  25                  30

```
Phe His Val Asn Leu Cys Gly Glu Glu Gln Glu Ala Asp Ala Ala
        35                  40                  45

Leu His Phe Asn Pro Arg Leu Asp Thr Ser Glu Val Val Phe Asn Thr
    50                  55                  60

Lys Gln Gln Gly Lys Trp Gly Arg Glu Glu Arg Gly Thr Gly Ile Pro
65                  70                  75                  80

Phe Gln Arg Gly Gln Pro Phe Glu Val Leu Ile Ile Thr Thr Glu Glu
                85                  90                  95

Gly Phe Lys Thr Val Ile Gly Asp Asp Glu Tyr Leu His Phe His His
                100                 105                 110

Arg Met Pro Ser Ser Asn Val Arg Ser Val Glu Val Gly Gly Asp Val
            115                 120                 125

Gln Leu His Ser Val Lys Ile Phe
        130                 135

<210> SEQ ID NO 8
<211> LENGTH: 136
<212> TYPE: PRT
<213> ORGANISM: Mouse

<400> SEQUENCE: 8

Met Ser Ala Thr His His Lys Thr Ser Leu Pro Gln Gly Val Arg Val
1               5                   10                  15

Gly Thr Val Met Arg Ile Arg Gly Leu Val Pro Asp Gln Ala Gly Arg
            20                  25                  30

Phe His Val Asn Leu Leu Cys Gly Glu Gln Gly Ala Asp Ala Ala
        35                  40                  45

Leu His Phe Asn Pro Arg Leu Asp Thr Ser Glu Val Val Phe Asn Thr
    50                  55                  60

Lys Gln Gln Gly Lys Trp Gly Arg Glu Glu Arg Gly Thr Gly Ile Pro
65                  70                  75                  80

Phe Gln Arg Gly Gln Pro Phe Glu Val Leu Leu Ile Ala Thr Glu Glu
                85                  90                  95

Gly Phe Lys Ala Val Val Gly Asp Asp Glu Tyr Leu His Phe His His
                100                 105                 110

Arg Leu Pro Pro Ala Arg Val Arg Leu Val Glu Val Gly Gly Asp Val
            115                 120                 125

Gln Leu His Ser Leu Asn Ile Phe
        130                 135

<210> SEQ ID NO 9
<211> LENGTH: 4
<212> TYPE: PRT
<213> ORGANISM: Human

<400> SEQUENCE: 9

Asn Phe Ser Leu
1

<210> SEQ ID NO 10
<211> LENGTH: 3
<212> TYPE: PRT
<213> ORGANISM: Human

<400> SEQUENCE: 10

Thr Val Lys
1
```

```
<210> SEQ ID NO 11
<211> LENGTH: 3
<212> TYPE: PRT
<213> ORGANISM: Human

<400> SEQUENCE: 11

Ser Gly Lys
  1

<210> SEQ ID NO 12
<211> LENGTH: 4
<212> TYPE: PRT
<213> ORGANISM: Human

<400> SEQUENCE: 12

Ser Leu His Asp
  1

<210> SEQ ID NO 13
<211> LENGTH: 4
<212> TYPE: PRT
<213> ORGANISM: Human

<400> SEQUENCE: 13

Thr Lys Leu Asp
  1

<210> SEQ ID NO 14
<211> LENGTH: 6
<212> TYPE: PRT
<213> ORGANISM: Human

<400> SEQUENCE: 14

Gly Ala Trp Gly Asn Gln
  1               5

<210> SEQ ID NO 15
<211> LENGTH: 6
<212> TYPE: PRT
<213> ORGANISM: Human

<400> SEQUENCE: 15

Gly Asn Gln Pro Ala Gly
  1               5

<210> SEQ ID NO 16
<211> LENGTH: 6
<212> TYPE: PRT
<213> ORGANISM: Human

<400> SEQUENCE: 16

Gly Gly Tyr Pro Gly Ala
  1               5

<210> SEQ ID NO 17
<211> LENGTH: 6
<212> TYPE: PRT
<213> ORGANISM: Human

<400> SEQUENCE: 17

Gly Ala Tyr Pro Gly Gln
  1               5

<210> SEQ ID NO 18
```

```
<211> LENGTH: 6
<212> TYPE: PRT
<213> ORGANISM: Human

<400> SEQUENCE: 18

Gly Ala Tyr Pro Gly Gln
 1               5

<210> SEQ ID NO 19
<211> LENGTH: 6
<212> TYPE: PRT
<213> ORGANISM: Human

<400> SEQUENCE: 19

Gly Ala Tyr Pro Gly Ala
 1               5

<210> SEQ ID NO 20
<211> LENGTH: 6
<212> TYPE: PRT
<213> ORGANISM: Human

<400> SEQUENCE: 20

Gly Ala Pro Gly Ala Tyr
 1               5

<210> SEQ ID NO 21
<211> LENGTH: 6
<212> TYPE: PRT
<213> ORGANISM: Human

<400> SEQUENCE: 21

Gly Ala Tyr Pro Gly Ala
 1               5

<210> SEQ ID NO 22
<211> LENGTH: 20
<212> TYPE: PRT
<213> ORGANISM: Human

<400> SEQUENCE: 22

Trp Gly Arg Glu Glu Arg Gln Ser Val Phe Pro Phe Glu Ser Gly Lys
 1               5                  10                  15

Pro Phe Lys Ile
            20

<210> SEQ ID NO 23
<211> LENGTH: 4
<212> TYPE: PRT
<213> ORGANISM: Human

<400> SEQUENCE: 23

Asn Ala Ser Arg
 1

<210> SEQ ID NO 24
<211> LENGTH: 3
<212> TYPE: PRT
<213> ORGANISM: Human

<400> SEQUENCE: 24

Ser Val Arg
 1
```

-continued

```
<210> SEQ ID NO 25
<211> LENGTH: 4
<212> TYPE: PRT
<213> ORGANISM: Human

<400> SEQUENCE: 25

Ser Leu Pro Glu
  1

<210> SEQ ID NO 26
<211> LENGTH: 6
<212> TYPE: PRT
<213> ORGANISM: Human

<400> SEQUENCE: 26

Gly Ile Arg Pro Gly Thr
  1               5

<210> SEQ ID NO 27
<211> LENGTH: 6
<212> TYPE: PRT
<213> ORGANISM: Human

<400> SEQUENCE: 27

Gly Ser Asp Ala Ala Leu
  1               5

<210> SEQ ID NO 28
<211> LENGTH: 20
<212> TYPE: PRT
<213> ORGANISM: Human

<400> SEQUENCE: 28

Trp Gly Arg Glu Glu Arg Gly Pro Gly Val Pro Phe Gln Arg Gly Gln
  1               5                  10                  15

Pro Phe Glu Val
             20
```